United States Patent
Chang et al.

(10) Patent No.: US 12,180,453 B2
(45) Date of Patent: Dec. 31, 2024

(54) SYSTEMS, DEVICES, AND METHODS FOR ELECTROPORATION WITHIN A CELL PROCESSING SYSTEM

(71) Applicant: Cellares Corporation, South San Francisco, CA (US)

(72) Inventors: Chihwei Chang, Alameda, CA (US); Wayne Grout, Oakland, CA (US)

(73) Assignee: Cellares Corporation, South San Francisco, CA (US)

( * ) Notice: Subject to any disclaimer, the term of this patent is extended or adjusted under 35 U.S.C. 154(b) by 0 days.

(21) Appl. No.: 18/611,632

(22) Filed: Mar. 20, 2024

(65) Prior Publication Data

US 2024/0318116 A1   Sep. 26, 2024

Related U.S. Application Data

(60) Provisional application No. 63/453,730, filed on Mar. 21, 2023.

(51) Int. Cl.
*C12M 1/42* (2006.01)
*C12M 1/00* (2006.01)
*C12M 1/36* (2006.01)

(52) U.S. Cl.
CPC ............ *C12M 35/02* (2013.01); *C12M 23/22* (2013.01); *C12M 41/48* (2013.01)

(58) Field of Classification Search
CPC ...... C12M 35/02; C12M 23/22; C12M 41/48; C12M 23/12; C12M 35/04; C12M 25/02;
(Continued)

(56) References Cited

U.S. PATENT DOCUMENTS

| 3,728,227 A | 4/1973 | Elson et al. |
| 4,234,023 A | 11/1980 | Sogi et al. |

(Continued)

FOREIGN PATENT DOCUMENTS

| CN | 104203333 A | 12/2014 |
| CN | 108660060 A | 10/2018 |

(Continued)

OTHER PUBLICATIONS

ChargePoint (2021). Aseptic split butterfly valve 10-6 sterility assurance, located at https://www.thechargepoint.com/products/aseptic-split-butterfly-valve-10-6-sterility-assurance/, 2 total pages.

(Continued)

*Primary Examiner* — Michael L Hobbs
(74) *Attorney, Agent, or Firm* — Cooley LLP

(57) ABSTRACT

The present disclosure relates to systems, devices, and methods for electroporating. In an embodiment, the present disclosure relates to an electroporation system, comprising at least one electroporation chamber, each electroporation chamber comprising a first electrode and a second electrode, a plurality of ports comprising an inlet port at a first portion of each electroporation chamber, and an outlet port at a second portion of each electroporation chamber, a fluid conduit arranged between the first electrode and the second electrode, the fluid conduit being in fluid communication with the inlet port and the outlet port, and an automated system for electroporation operatively connected to the first electrode and the second electrode of the at least one electroporation chamber.

27 Claims, 18 Drawing Sheets

(58) Field of Classification Search
CPC .... C12N 13/00; C12N 15/87; C12N 15/8207; C12N 15/8206; C12N 23/12; A61N 1/306; A61K 8/00; A61K 38/00
See application file for complete search history.

(56) References Cited

U.S. PATENT DOCUMENTS

| | | |
|---|---|---|
| 4,696,902 A | 9/1987 | Bisconte |
| 4,839,292 A | 6/1989 | Cremonese |
| 4,911,833 A | 3/1990 | Schoendorfer et al. |
| 5,058,619 A | 10/1991 | Zheng |
| 5,656,491 A | 8/1997 | Cassani et al. |
| 6,649,419 B1 | 11/2003 | Anderson |
| 6,891,182 B2 | 5/2005 | Watari et al. |
| 7,550,287 B2 | 6/2009 | Hibino et al. |
| 7,745,209 B2 | 6/2010 | Martin et al. |
| 7,816,128 B2 | 10/2010 | Nakashima et al. |
| 8,158,426 B2 | 4/2012 | Wilson et al. |
| 8,158,427 B2 | 4/2012 | Wilson et al. |
| 8,168,432 B2 | 5/2012 | Wilson et al. |
| 8,273,572 B2 | 9/2012 | Martin et al. |
| 8,415,144 B2 | 4/2013 | Wilson et al. |
| 8,440,458 B2 | 5/2013 | Zijlstra et al. |
| 8,470,589 B2 | 6/2013 | Martin et al. |
| 8,492,140 B2 | 7/2013 | Smith et al. |
| 8,546,142 B2 | 10/2013 | Martin et al. |
| 8,697,443 B2 | 4/2014 | Wilson et al. |
| 8,727,132 B2 | 5/2014 | Miltenyi et al. |
| 8,809,044 B2 | 8/2014 | Wilson |
| 8,846,399 B2 | 9/2014 | Martin et al. |
| 8,956,860 B2 | 2/2015 | Vera et al. |
| 9,040,290 B2 | 5/2015 | Martin et al. |
| 9,045,721 B2 | 6/2015 | Martin et al. |
| 9,080,149 B2 | 7/2015 | Bosio et al. |
| 9,255,243 B2 | 2/2016 | Wilson et al. |
| 9,279,099 B2 | 3/2016 | Okano et al. |
| 9,290,730 B2 | 3/2016 | Martin et al. |
| 9,410,114 B2 | 8/2016 | Wilson et al. |
| 9,441,192 B2 | 9/2016 | Wilson et al. |
| 9,499,780 B2 | 11/2016 | Smith et al. |
| 9,534,195 B2 | 1/2017 | Smith et al. |
| 9,556,485 B2 | 1/2017 | Lin et al. |
| 9,567,565 B2 | 2/2017 | Vera et al. |
| 9,597,355 B2 | 3/2017 | Magnant |
| 9,625,463 B2 | 4/2017 | Miltenyi et al. |
| 9,701,932 B2 | 7/2017 | Smith et al. |
| 9,732,317 B2 | 8/2017 | Wilson |
| 9,783,768 B2 | 10/2017 | Larcher et al. |
| 9,845,451 B2 | 12/2017 | Martin et al. |
| 10,047,342 B2 | 8/2018 | Eibl et al. |
| 10,053,663 B2 | 8/2018 | Kabaha et al. |
| 10,119,970 B2 | 11/2018 | Miltenyi et al. |
| 10,131,876 B2 | 11/2018 | Kaiser et al. |
| 10,253,316 B2 | 4/2019 | Masquelier et al. |
| 10,294,658 B2 | 5/2019 | Scannon et al. |
| 10,323,258 B2 | 6/2019 | Bernate et al. |
| 10,329,559 B1 | 6/2019 | Masquelier et al. |
| 10,385,307 B2 | 8/2019 | Rowley et al. |
| 10,421,959 B1 | 9/2019 | Masquelier et al. |
| 10,508,288 B1 | 12/2019 | Bernate et al. |
| 10,519,437 B1 | 12/2019 | Masquelier et al. |
| 10,533,156 B2 | 1/2020 | Vera et al. |
| 10,584,333 B1 | 3/2020 | Masquelier et al. |
| 10,584,334 B1 | 3/2020 | Masquelier et al. |
| 10,588,994 B2 | 3/2020 | Kawamura et al. |
| 10,620,212 B2 | 4/2020 | Miltenyi et al. |
| 10,689,669 B1 | 6/2020 | Feldman et al. |
| 10,705,090 B2 | 7/2020 | Miltenyi et al. |
| 10,705,091 B2 | 7/2020 | Miltenyi et al. |
| 10,723,986 B2 | 7/2020 | Smith et al. |
| 10,724,043 B2 | 7/2020 | Sixto et al. |
| 10,844,338 B1 | 11/2020 | Smith et al. |
| 11,161,111 B2 | 11/2021 | Kabaha et al. |
| 11,198,845 B2 | 12/2021 | Parietti et al. |
| 11,371,018 B2 | 6/2022 | Shi et al. |
| 11,376,587 B2 | 7/2022 | Thakkar et al. |
| 11,447,745 B2 | 9/2022 | Shi et al. |
| 11,701,654 B2 | 7/2023 | Azersky et al. |
| 11,786,896 B2 | 10/2023 | Thakkar et al. |
| 11,826,756 B2 | 11/2023 | Azersky et al. |
| 11,872,557 B2 | 1/2024 | Biz et al. |
| 2003/0030272 A1 | 2/2003 | Johnson et al. |
| 2005/0070018 A1* | 3/2005 | Johnson ............... C12M 35/02 435/173.6 |
| 2005/0186671 A1 | 8/2005 | Cannon et al. |
| 2006/0194193 A1 | 8/2006 | Tsuruta et al. |
| 2006/0257999 A1 | 11/2006 | Chang et al. |
| 2007/0185472 A1 | 8/2007 | Baumfalk et al. |
| 2008/0057568 A1 | 3/2008 | Kan et al. |
| 2008/0176318 A1 | 7/2008 | Wilson et al. |
| 2009/0042281 A1 | 2/2009 | Chang et al. |
| 2009/0247417 A1 | 10/2009 | Haas et al. |
| 2010/0130732 A1 | 5/2010 | Chung et al. |
| 2011/0003380 A1 | 1/2011 | Miltenyi et al. |
| 2011/0223064 A1 | 9/2011 | Katsumi et al. |
| 2012/0138156 A1 | 6/2012 | Hofman et al. |
| 2012/0293338 A1 | 11/2012 | Chaffey et al. |
| 2013/0078624 A1 | 3/2013 | Holmes et al. |
| 2013/0115617 A1 | 5/2013 | Wilson |
| 2014/0309795 A1 | 10/2014 | Norton et al. |
| 2015/0307829 A1 | 10/2015 | Dedry et al. |
| 2016/0208216 A1 | 7/2016 | Vera et al. |
| 2016/0303563 A1 | 10/2016 | Granier et al. |
| 2016/0320381 A1 | 11/2016 | Holmes et al. |
| 2016/0320422 A1 | 11/2016 | Fritchie et al. |
| 2017/0307502 A1 | 10/2017 | Mason et al. |
| 2017/0313977 A1 | 11/2017 | Wilson |
| 2017/0321226 A1 | 11/2017 | Gill et al. |
| 2017/0348525 A1* | 12/2017 | Sano ............... A61B 18/1206 |
| 2017/0362554 A1 | 12/2017 | Martin et al. |
| 2018/0051243 A1 | 2/2018 | Hogan et al. |
| 2018/0078935 A1 | 3/2018 | Hung et al. |
| 2018/0196918 A1 | 7/2018 | Sadowski et al. |
| 2019/0212233 A1 | 7/2019 | Jovanovich et al. |
| 2019/0275519 A1 | 9/2019 | Castillo et al. |
| 2019/0292510 A1 | 9/2019 | Tandon et al. |
| 2019/0316120 A1 | 10/2019 | Masquelier et al. |
| 2019/0330579 A1 | 10/2019 | Guenat et al. |
| 2020/0025782 A1 | 1/2020 | Ahlfors |
| 2020/0048599 A1* | 2/2020 | Firouzi ............... C12N 13/00 |
| 2020/0095550 A1 | 3/2020 | Vera et al. |
| 2020/0159198 A1 | 5/2020 | Kapre et al. |
| 2020/0292552 A1 | 9/2020 | Miltenyi et al. |
| 2020/0353004 A1 | 11/2020 | Nowak et al. |
| 2020/0368411 A1 | 11/2020 | Camisani et al. |
| 2020/0399578 A1* | 12/2020 | Corso ............... C12M 35/02 |
| 2020/0406221 A1 | 12/2020 | Dabrowski et al. |
| 2021/0032583 A1 | 2/2021 | Smith et al. |
| 2021/0047668 A1 | 2/2021 | Dabrowski et al. |
| 2021/0079344 A1 | 3/2021 | Bosio et al. |
| 2021/0147807 A1 | 5/2021 | Lickert et al. |
| 2021/0253997 A1 | 8/2021 | Wilson |
| 2021/0269755 A1 | 9/2021 | Smith et al. |
| 2021/0283565 A1 | 9/2021 | Gerlinghaus et al. |
| 2021/0301239 A1 | 9/2021 | Natsume et al. |
| 2021/0324318 A1 | 10/2021 | Parietti et al. |
| 2021/0354104 A1 | 11/2021 | Pesch et al. |
| 2022/0002652 A1 | 1/2022 | Patrick et al. |
| 2022/0003796 A1 | 1/2022 | Ahlfors |
| 2022/0047862 A1* | 2/2022 | Chang ............... C12M 35/02 |
| 2022/0121181 A1 | 4/2022 | Sobalvarro et al. |
| 2022/0143610 A1 | 5/2022 | Biz et al. |
| 2022/0150650 A1 | 5/2022 | Rucker |
| 2022/0259546 A1 | 8/2022 | Blanchard |
| 2022/0325219 A1 | 10/2022 | Parietti et al. |
| 2022/0347683 A1 | 11/2022 | Thakkar et al. |
| 2023/0149922 A1 | 5/2023 | Thakkar et al. |
| 2023/0321650 A1 | 10/2023 | Azersky et al. |
| 2023/0415154 A1 | 12/2023 | Pesch et al. |
| 2023/0415155 A1 | 12/2023 | Biz et al. |
| 2024/0165613 A1 | 5/2024 | Azersky et al. |
| 2024/0254426 A1 | 8/2024 | Elpel et al. |
| 2024/0255537 A1 | 8/2024 | Malleo et al. |

(56) References Cited

U.S. PATENT DOCUMENTS

FOREIGN PATENT DOCUMENTS

| | | |
|---|---|---|
| EP | 0246912 A2 | 11/1987 |
| EP | 0991389 A1 | 4/2000 |
| EP | 0824380 B1 | 1/2002 |
| EP | 3134512 B1 | 1/2019 |
| EP | 2809449 B1 | 10/2019 |
| EP | 3359294 B1 | 5/2020 |
| GB | 2268187 A | 1/1994 |
| JP | 2007325586 A | 12/2007 |
| KR | 20130018286 A | 2/2013 |
| WO | WO-9320440 A1 | 10/1993 |
| WO | WO-2006102416 A2 | 9/2006 |
| WO | WO-2006112870 A1 | 10/2006 |
| WO | WO-2006118282 A1 | 11/2006 |
| WO | WO-2007139742 A1 | 12/2007 |
| WO | WO-2009072003 A2 | 6/2009 |
| WO | WO-2017041051 A1 | 3/2017 |
| WO | WO-2017123663 A1 | 7/2017 |
| WO | WO-2018015561 A1 | 1/2018 |
| WO | WO-2018102471 A1 | 6/2018 |
| WO | WO-2020009700 A1 | 1/2020 |
| WO | WO-2020014264 A1 | 1/2020 |
| WO | WO-2021168368 A1 | 8/2021 |
| WO | WO-2021183687 A2 | 9/2021 |
| WO | WO-2021212124 A1 | 10/2021 |
| WO | WO-2024112702 A1 | 5/2024 |
| WO | WO-2024152008 A1 | 7/2024 |

OTHER PUBLICATIONS

CPC (2014). "6 traits of non-spill: How quick disconnect couplings evolved for low-pressure fluid handling," White Paper 8004, 4 total pages.
CPC (2014). "How single-use connections advance aseptic processing: Increased process flexibility and reliability, reduced costs," White Paper 7004, 6 total pages.
CPC (2018). Comparison Guide: Tube Welders and Aseptic Connectors, Technical Guide 7009, 3 total pages.
EMD Millipore (2015). "Lynx® S2S Connector—Low temperature compatibility (−80"C)," 4 total pages.
Final Office Action mailed on Apr. 28, 2022, for U.S. Appl. No. 17/198,134, filed Mar. 10, 2021, 11 pages.
Final Office Action mailed on Apr. 28, 2022, for U.S. Appl. No. 17/331,554, filed May 26, 2021, 16 pages.
Final Office Action mailed on Jul. 31, 2023, for U.S. Appl. No. 17/331,554, filed May 26, 2021, 19 pages.
Final Office Action mailed on Mar. 31, 2023, for U.S. Appl. No. 17/579,478, filed Jan. 19, 2022, 8 pages.
Garcia et al., "Microfluidic Screening of Electric Fields for Electroporation" Sci Rep. Feb. 19, 2016; 6:21238. pp. 1-11.
Genetic Engineering & Biotechnology News (2006). "Thermal welding for sterile connections," located at https://www.genengnews.com/magazine/47/thermal-welding-for-sterile-connections/, 5 total pages.
International Search Report and Written Opinion for International Application No. PCT/US2023/080593 dated Mar. 21, 2024, 12 pages.
International Search Report mailed on Oct. 13, 2021, for PCT Application No. PCT/US2021/021773, filed on Mar. 10, 2021, 13 pages.
Jain, S. et al. (2011). "The complete automation of cell culture: improvements for high-throughput and high-content screening," J. Biomol. Screen 16:932-939.
Kato, R. et al. (2010). "A Compact, Automated Cell Culture System for Clinical Scale Cell Expansion from Primary Tissues," Tissue Engineering: Part C 16:947-956.
Kempner, M.E. and Felder, R.A., "A review of cell culture automation". JALA: Journal of the Association for Laboratory Automation (Apr. 2002); 7(2): 56-62.

Kino-Oka, M. et al. (2005). "Bioreactor Design for Successive Culture of Anchorage-Dependent Cells Operated in an Automated Manner," Tissue Engineering 11:535-545.
Knoll, A. et al. (2004). "Flexible automation of cell culture and tissue engineering tasks," Biotechnol. Prog. 20:1825-1835.
Lutkemeyer, D. et al. (2000). "First steps in robot automation of sampling and sample management during cultivation of mammalian cells in pilot scale," Biotechnol. Prog. 16:822-828.
MEDInstill (2021). INTACT™ Connectors, located at https://www.medinstill.com/intactconnectors.php, 1 total page.
Millipore® (2020). "Technical Brief—Choosing the right sterile connector based on design and sterility test results," 4 total pages.
Millipore Sigma (2020). "Lynx® CDR Connectors," Datasheet, 4 total pages.
Millipore Sigma (2021). Lynx® CDR Connectors, located at https://www.emdmillipore.com/US/en/product/Lynx-CDR-Connectors,MM_NF-C188801, 2 total pages.
Non Final Office Action for U.S. Appl. No. 17/579,478 mailed on Dec. 22, 2022, 7 pages.
Non-Final Office Action for U.S. Appl. No. 17/198,134, dated Jun. 26, 2023, 15 pages.
Non-Final Office Action for U.S. Appl. No. 17/331,554 dated Apr. 24, 2024, 17 pages.
Non-Final Office Action mailed on Dec. 3, 2021, for U.S. Appl. No. 17/331,556, filed May 26, 2021, 9 pages.
Non-Final Office Action mailed on Feb. 3, 2022, for U.S. Appl. No. 17/198,134, filed Mar. 10, 2021, 5 pages.
Non-Final Office Action mailed on Mar. 16, 2023, for U.S. Appl. No. 17/331,554, filed May 26, 2021, 16 pages.
Non-Final Office Action mailed on Oct. 28, 2021, for U.S. Appl. No. 17/331,554, filed May 26, 2021, 11 pages.
Non-Final Office Action mailed on Oct. 6, 2021, for U.S. Appl. No. 17/198, 34, filed Mar. 10, 2021, 7 pages.
Non-Final Office Action mailed on Sep. 13, 2023, for U.S. Appl. No. 18/141,329, filed Apr. 28, 2023, 7 pages.
Notice of Allowance for U.S. Appl. No. 17/198,134 dated Apr. 11, 2024, 9 pages.
Notice of Allowance for U.S. Appl. No. 17/992,784, dated Mar. 22, 2023, 7 pages.
Notice of Allowance mailed on Jul. 18, 2023, for U.S. Appl. No. 17/849,422, filed Jun. 24, 2022, 8 pages.
Notice of Allowance mailed on Jul. 25, 2023, for U.S. Appl. No. 17/579,478, filed Jan. 19, 2022, 8 pages.
Notice of Allowance mailed on Jun. 8, 2023, for U.S. Appl. No. 17/849,422, filed Jun. 24, 2022, 8 pages.
Notice of Allowance mailed on Mar. 1, 2022, for U.S. Appl. No. 17/331,556, filed May 26, 2021, 8 pages.
Notice of Allowance mailed on Oct. 4, 2023, for U.S. Appl. No. 18/141,329, filed Apr. 28, 2023, 8 pages.
Qu, B., et al., "Droplet Electroporation in Microfluidics for Efficient Cell Transformation with or without Cell Wall Removal," Lab Chip, 2012, vol. 12, pp. 4483-4488.
Saint Gobain (2017). "Pure-Fit® SC—Secure aseptic connections," Brochure, 5 total pages.
Sartorius Stedim Biotech (2011). "Opta® SFT," 4 total pages.
Schwartz C., "Optimizing Cell Separation with Beckman Coulter's Centrifugal Elutriation System," Beckmann Coulter Life Sciences (2014) 6 total pages.
SeriesLock™ (2021). Features and Specifications, located at https://serieslock.com/, 5 total pages.
Shi, Y. et al. (1992). "Performance of Mammalian Cell Culture Bioreactor with a New Impeller Design," Biotechnology and Bioengineering 40:260-270.
Steris (2018). "A compilation of material compatibilities with vaporized hydrogen peroxide," 2 total pages.
Steris (2018). "Sterility assurance levels (SALS): Irradiation," 3 total pages.
Steris (2020). "Overview of sterilization technology comparison," 1 total page.
Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.

(56) References Cited

OTHER PUBLICATIONS

Written Opinion of the International Searching Authority mailed on Oct. 13, 2021, for PCT Application No. PCT/US2021/021773, filed on Mar. 10, 2021, 20 pages.
International Search Report and Written Opinion for PCT Application No. PCT/US2024/011486 dated May 24, 2024, 12 pages.
Invitation to Pay Additional Fees for International Application No. PCT/US2024/022079 dated Jul. 17, 2024, 19 pages.
Invitation to Pay Additional Fees for International Application No. PCT/US2024/025064, mailed Jul. 16, 2024, 12 pages.
Non-Final Office Action for U.S. Appl. No. 18/652,602 mailed Jul. 17, 2024, 30 pages.
Non-Final Office Action for U.S. Appl. No. 18/731,095 mailed Aug. 8, 2024, 24 pages.
Pharma Japan, "Astellas Set to Cut Development Time with Cell Culture Robot, Eyes 4 Billion Yen Profit per Product" Aug. 9, 2023, 3 pages.

* cited by examiner

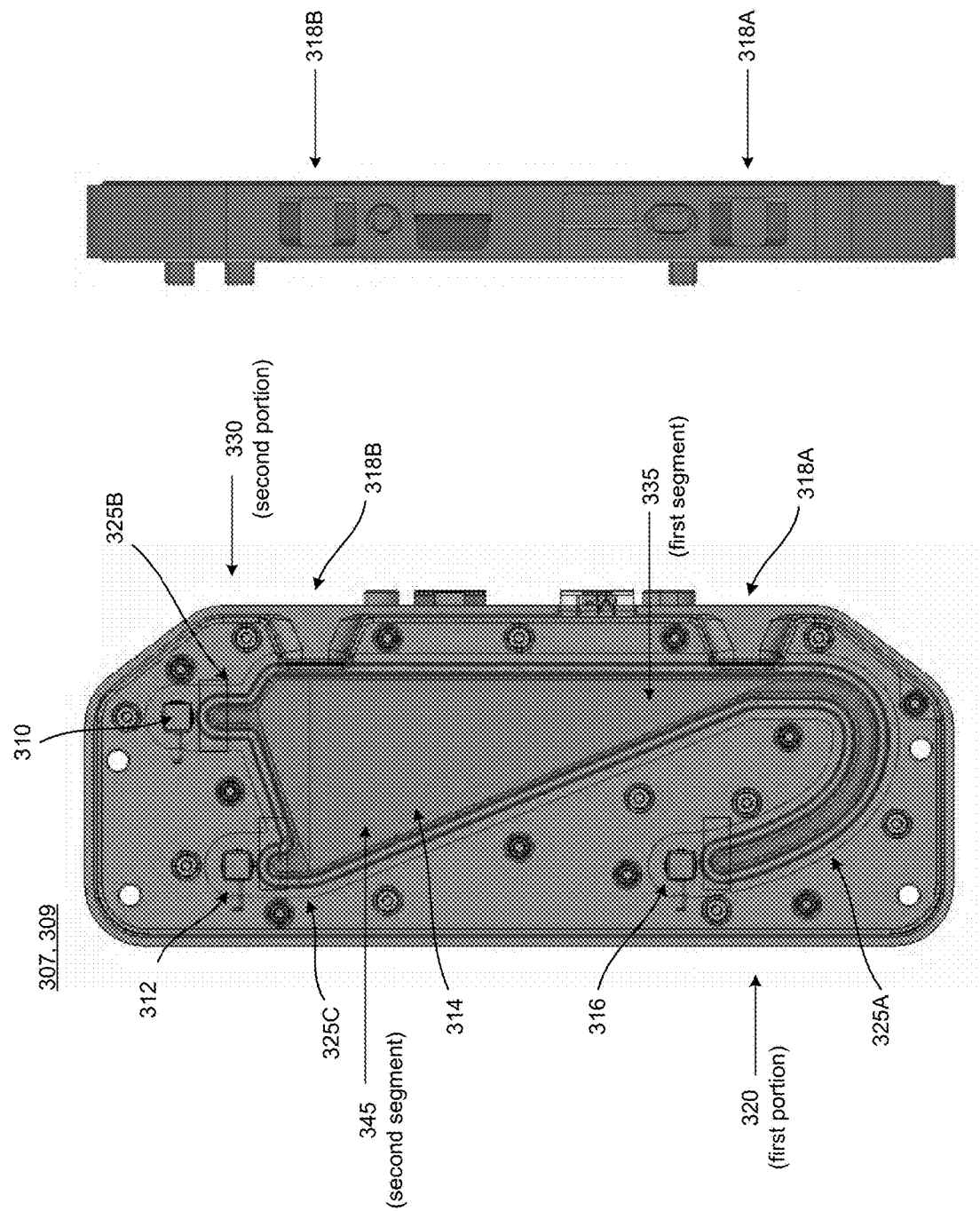

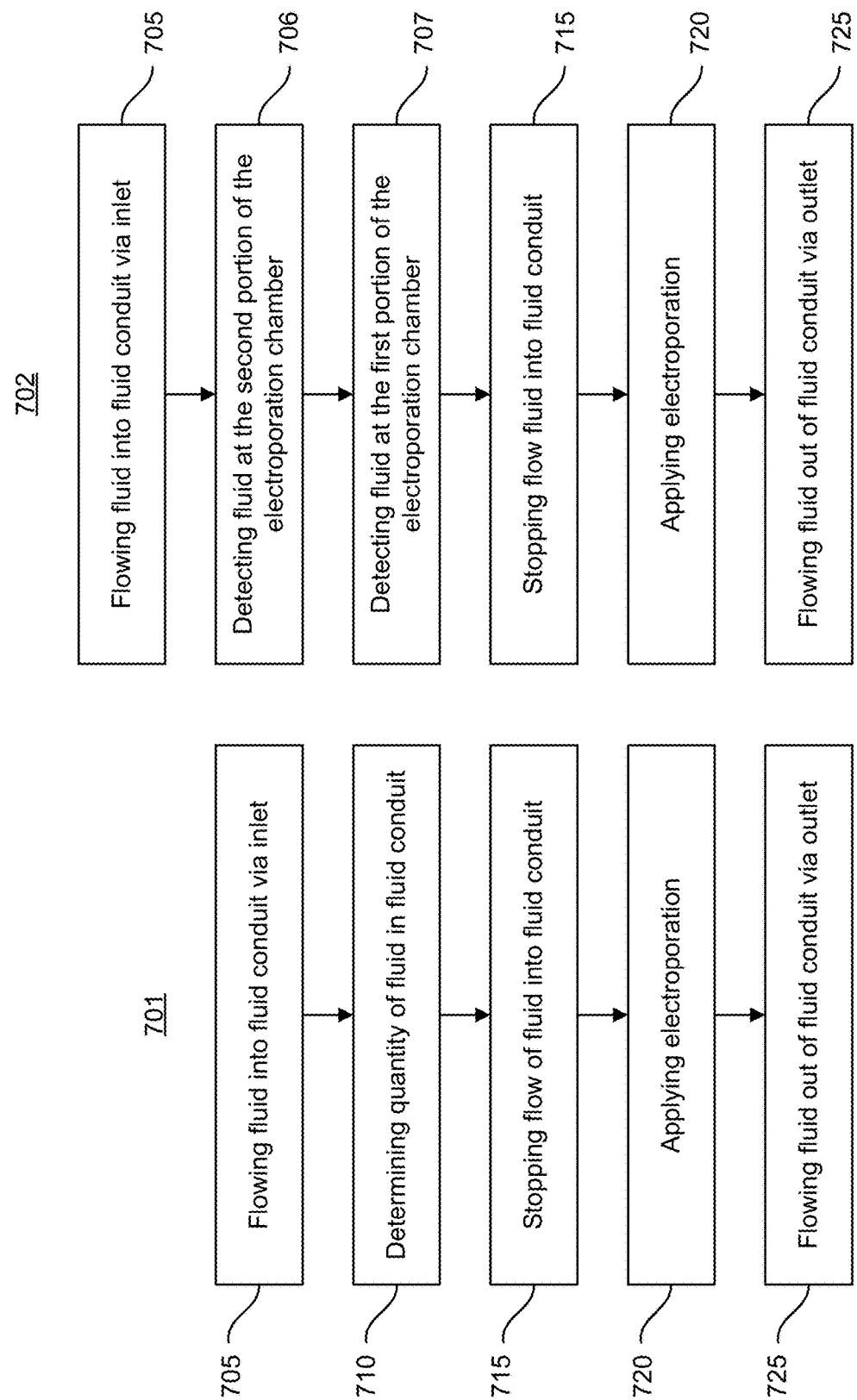

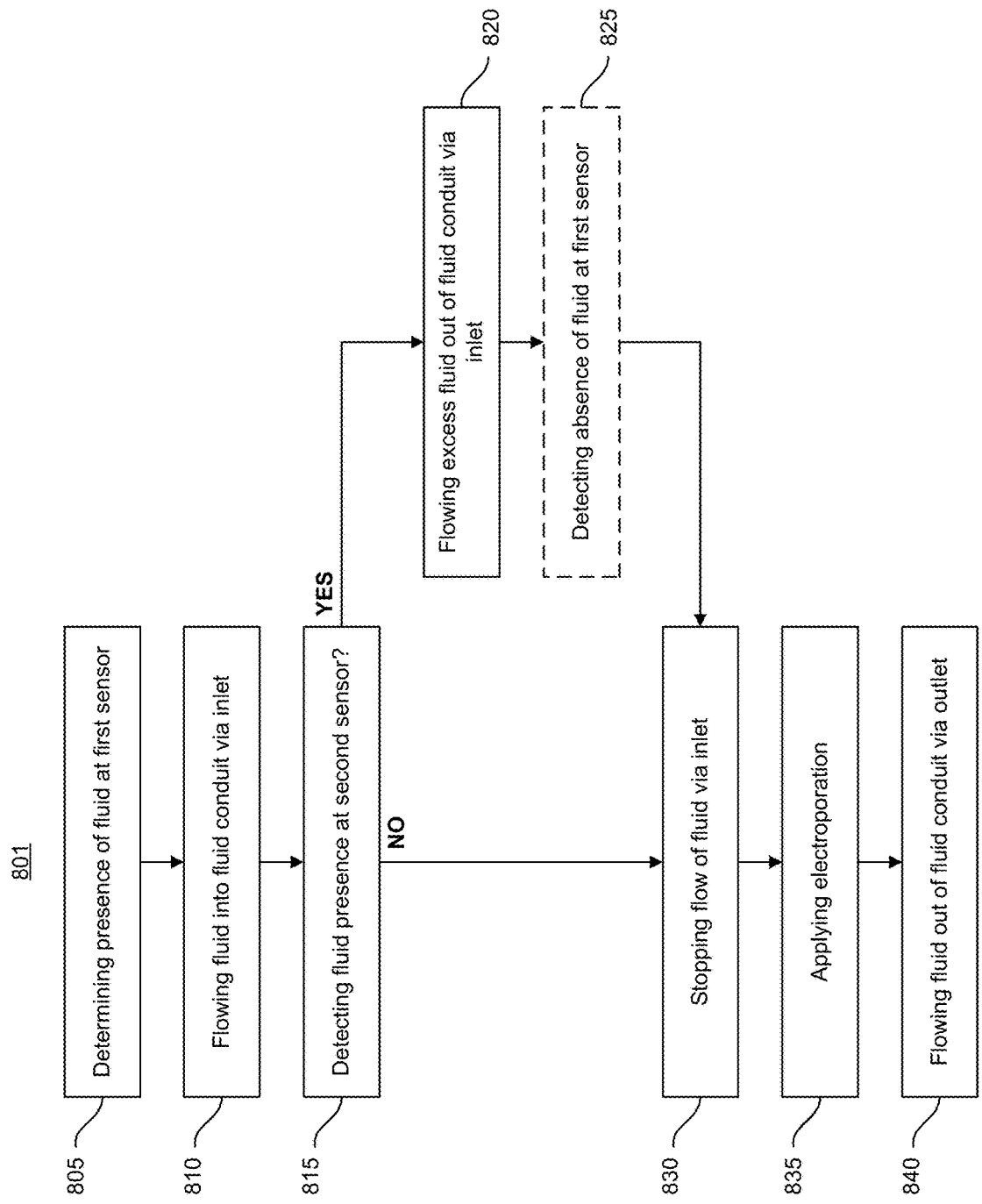

SYSTEMS, DEVICES, AND METHODS FOR ELECTROPORATION WITHIN A CELL PROCESSING SYSTEM

CROSS REFERENCE TO RELATED APPLICATIONS

This application claims priority to U.S. Provisional Patent Application No. 63/453,730, filed Mar. 21, 2023, the content of which is hereby incorporated in its entirety by this reference.

TECHNICAL FIELD

The present disclosure relates to systems, devices, and methods for electroporation, for example, electroporation within a cell processing system.

BACKGROUND

Electroporation applies an electric field to cells to open nano- to micron-scale pores in the cell membrane, thereby increasing permeability of the cell membrane and allowing chemicals, drugs, and/or biological matter (e.g., DNA) into the cell. An electroporation process can include generating the pores, stabilizing the pores, and sealing the pores, in a process referred to as reversible electroporation. Current electroporation devices are configured to apply electroporation to a specific volume of cell solution. Proper application of electroporation energy requires adjustments to the electrical parameters based on the volume of solution. Some electroporation devices may be unable to accurately measure the volume of cell solution prior to the application of electrical energy. Some devices may be unable to remove a specific amount of cell solution prior to application of the electrical energy, as would be necessary in the case of overfilling the device. Some electroporation devices are unable to provide electrical energy levels sufficient to accommodate large volumes of cell solution. Some electroporation devices may be unable to apply electrical energy to substantially all of the cells contained within the device. Additionally, electroporation devices used by those skilled in the art may only be able to process a single container of cell solution at a time. Accordingly, some chambers may be unable to support multiple devices that each contain a cell solution, which increases processing time and reduces clinical efficiency.

Accordingly, additional methods for electroporation are desirable.

SUMMARY

The present disclosure relates generally to systems, devices, and methods for electroporation within an automated cell processing system. In general, the electroporation devices disclosed herein may include an electroporation chamber. In some variations, the electroporation chamber may include a first electrode and a second electrode, a plurality of ports having an inlet port at a first portion of the electroporation chamber, and an outlet port at a second portion of the electroporation chamber, a fluid conduit arranged between the first electrode and the second electrode, the fluid conduit being in fluid communication with the inlet port and the outlet port, and at least one window disposed on a wall of the electroporation chamber. The distance between the first and second electrodes may be any suitable distance, and in some variations, the distance may be between about 0.5 mm and about 5 mm. The electroporation chamber may further include a first housing and a second housing, where the first electrode, the fluid conduit, and the second electrode may be positioned between the first housing and the second housing. In some variations, the segment of the fluid conduit may be proximate the first portion of the electroporation chamber. Additionally, or alternatively, the segment of the fluid conduit may be proximate the second portion of the electroporation chamber. In some variations, the at least one window may include a first window and a second window, the first window having a view to a first segment of the fluid conduit and the second window having a view to a second segment of the fluid conduit. Moreover, in some variations, each of the plurality of ports may extend through the first electrode and/or the second electrode.

In some variations, the plurality of ports may further include a vent port in fluid communication with the fluid conduit and arranged at the first portion of the electroporation chamber. The fluid conduit may be in fluid communication with each of the plurality of ports via auxiliary channels extending therefrom. Each of the auxiliary channels may be fluidically coupled the fluid conduit and a respective one of the plurality of ports. In some variations, an auxiliary channel of the auxiliary channels fluidically coupling the fluid conduit to the outlet port may be curvilinear. Further, in some variations, the at least one window may include a first window and a second window, the first window having a view to a first segment of the fluid conduit and the second window having a view to a second segment of the fluid conduit, where second window may be proximate the auxiliary channel in fluid communication with the outlet port. Additionally, an auxiliary channel in fluid communication with the outlet port may be curvilinear, and the second window may be proximate the curvilinear auxiliary channel. In some variations, the second window may be proximate a base of the curvilinear auxiliary channel. In some variations, the first window may be proximate the auxiliary channel in fluid communication with the vent port. Further, the first window may be proximate a base of the auxiliary channel in fluid communication with the vent port. Moreover, in some variations, the inlet port arranged at the first portion of the electroporation chamber may be further arranged toward a first side wall of the electroporation chamber, and the vent port arranged at the first portion of the electroporation chamber may be further arranged toward a second side wall of the electroporation chamber.

In some variations, the fluid conduit may have a volume defined by a distance between the first electrode and the second electrode. The volume of the fluid conduit may be between about 0.5 µL to about 2.5 mL. Moreover, in some variations, along an axis defined from the first portion of the electroporation chamber to the second portion of the electroporation chamber, the fluid conduit may have a triangular cross-section.

Also described here are systems for electroporation. In some variations, the systems may include an output stage and a multiplexer configured to direct at least a portion of the electric load to at least one of a first electroporation chamber and a second electroporation chamber. Further, in some variations, excess charge within the capacitance bank may be dumped via the charging-discharging circuit.

In some variations, the system may further include a charging-discharging circuit and a capacitance bank chargeable via a high voltage direct current to direct current converter. The capacitance bank may store about 4.5 mF.

In some variations, the system may further include an integrated pulsing module that opens or closes a supply path of the electric load to the output stage. The integrated pulsing module may support a pulse amperage up to about 800 A for a pulse length of about 1 ms.

In other variations, the systems for electroporation described herein may include at least one electroporation chamber, each electroporation chamber comprising a first electrode and a second electrode, a plurality of ports comprising an inlet port at a first portion of each electroporation chamber, and an outlet port at a second portion of each electroporation chamber, a fluid conduit arranged between the first electrode and the second electrode, the fluid conduit being in fluid communication with the inlet port and the outlet port, and an automated system for electroporation operatively connected to the first electrode and the second electrode of the at least one electroporation chamber. In some variations, an output from the system may produce an electric field of between about 1.0 kV/cm to about 3 kV/cm within the fluid conduit of at least one of the first electroporation chamber and the second electroporation chamber.

In some variations, the system may further include at least one window disposed on a wall of each electroporation chamber and providing a view to a corresponding segment of the fluid conduit of the electroporation chamber. The at least one window may include a first window and a second window, the first window having a view to a first segment of the fluid conduit and the second window having a view to a second segment of the fluid conduit. In some variations, the system may further include at least one sensor configured to view the at least one window. Each of the plurality of ports may extend through the first electrode and/or the second electrode.

Moreover, in some variations, the system may further include processing circuitry configured to, for each of the at least one electroporation chamber: generate a first signal to flow a cell solution into the fluid conduit via the inlet port, generate a second signal, based on data received from the at least one sensor, to stop the flow of the cell solution into the fluid conduit via the inlet port, generate a third signal to apply, via the automated system for electroporation, an electric field within the fluid conduit for a pre-determined duration, and generate a fourth signal to flow the cell solution out of the fluid conduit via the outlet port. The plurality of ports may further include a vent port in fluid communication with the fluid conduit and arranged at the first portion of each electroporation chamber. In some variations, the fourth signal generated by the processing circuitry may be configured to cause a fluid pump to flow the cell solution out of the fluid conduit by purging the fluid conduit with air via the vent port. The further comprising a fluid pump, wherein the first signal, the second signal, and the fourth signal are transmitted to the fluid pump.

In some variations, the system may have an output stage that switches a polarity of an electric load and a multiplexer configured to direct at least a portion of the electric load to at least one of a first electroporation chamber and a second electroporation chamber. Additionally, the automated system for electroporation may further include a charging-discharging circuit, and a capacitance bank chargeable via a high voltage direct current to direct current converter. Further, the system may further include comprising an integrated pulsing module that may open or close a supply path of the electric load to the output stage. In some variations, the integrated pulsing module may support a pulse amperage up to about 800 A for a pulse length of about 1 ms.

Methods of electroporating cells are also described herein. In some variations, the methods may include flowing a cell solution into a fluid conduit of an electroporation chamber via an inlet port of an electroporation chamber, detecting, via at least one window in a wall of the electroporation chamber, a presence of the cell solution at a second portion of the electroporation chamber, ceasing flow of the cell solution into the fluid conduit, applying an electric field to the cell solution within the fluid conduit for a pre-determined duration via a first electrode of the electroporation chamber and a second electrode of the electroporation chamber, and flowing the cell solution out of the fluid conduit via the outlet port.

In some variations, at least one window may be a second window arranged proximate the outlet port. In some variations, the method may further include detecting, via a first window and after detecting the presence of the cell solution at the second portion of the electroporation chamber via the second window, a presence of the cell solution at the first portion of the electroporation chamber, where the electric field may be applied after detecting the presence of the cell solution at the first portion of the electroporation chamber. Detecting the presence of the cell solution at the first portion of the electroporation chamber may include detecting a presence of the cell solution proximate a vent port in fluid communication with the fluid conduit and arranged at the first portion of the electroporation chamber. Detecting the presence of the cell solution at the second end of the electroporation chamber may include detecting a presence of the cell solution proximate an auxiliary channel extending from the fluid conduit, the auxiliary channel being in fluid communication with the fluid conduit and the outlet port. Moreover, in some variations, flowing the cell solution out of the fluid conduit via the outlet port may include purging the fluid conduit with air via a vent port in fluid communication with the fluid conduit and arranged at the first portion of the electroporation chamber.

In other variations, the methods of electroporating cells described herein may include positioning, by a robot, a cartridge comprising cells within an electroporation instrument of a workcell, flowing a solution of the cells into an electroporation chamber of the cartridge, the electroporation chamber being within an electroporation module couplable the electroporation instrument, detecting, by the electroporation instrument and via at least one window disposed on the electroporation chamber, a presence of the cell solution within a portion of the electroporation chamber, ceasing flow of the cell solution into the electroporation chamber, applying an electric field to the cell solution via a first electrode of the electroporation chamber and a second electrode of the electroporation chamber, and flowing the cell solution out of the electroporation chamber.

Additional embodiments, features, and advantages of the invention will be apparent from the following detailed description and through practice of the invention.

BRIEF DESCRIPTION OF THE DRAWINGS

FIG. 3E is a rendering of an aspect of an illustrative electroporation chamber of a cartridge.

FIG. 3F is a rendering of an aspect of an illustrative electroporation chamber of a cartridge.

FIG. 7A, FIG. 7B, and FIG. 7C are flowcharts of illustrative variations of an electroporation method.

FIG. 8A and FIG. 8B are flowcharts of illustrative variations of an electroporation method.

DETAILED DESCRIPTION

Figure 1A:
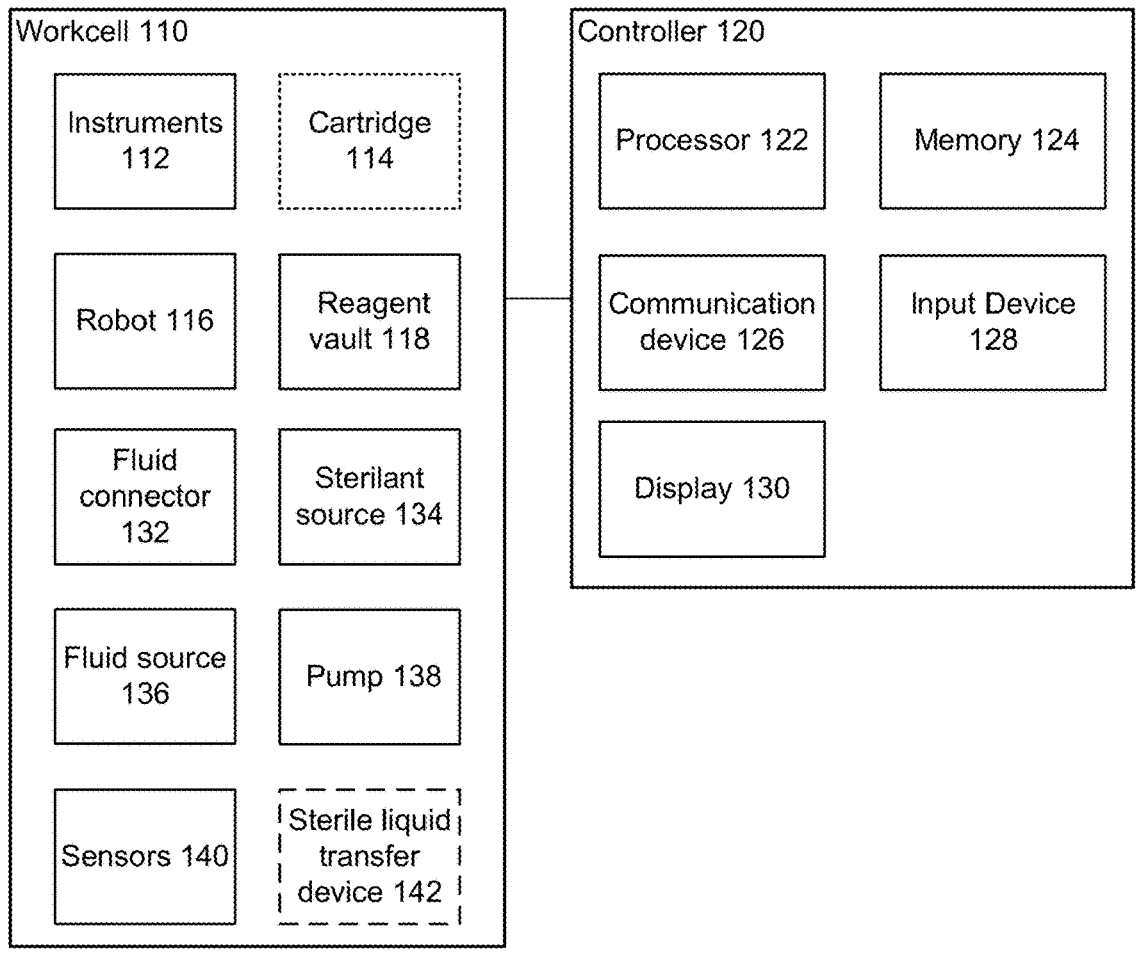
FIG. 1A is a block diagram of an illustrative variation of a cell processing system.

Electroporation typically comprises applying an electric field to cells to induce opening of nano- and/or micro-scale pores on the cells' membranes in order to increase the permeability of the cells' membranes. In turn, the pores allow chemicals, drugs, and/or DNA to be introduced into the cells. An exemplary process of electroporation includes generating the pores, stabilizing the pores, and sealing the pores.

During the electroporation process, host cells and selected molecules may be suspended in a conductive solution, and an electrical circuit is closed around the mixture. An electrical pulse is discharged through the cell suspension. This disturbs the phospholipid bilayer of the membrane and results in the formation of temporary pores. The electric potential across the cell membrane simultaneously rises to allow charged molecules like DNA, RNA, etc. to be driven across the membrane through the pores in a manner similar to electrophoresis.

More specifically, when an electrical field is applied across cells, the induced transmembrane potential accumulates across the cell membrane and opens pores on both sides of the cell along the direction of the electric field. Because of the conductivity and the dielectric constant difference between the inside and the outside of the cells, an electric field will not be present within the cells. Accordingly, DNA, RNA, and/or proteins will stick into the pores of the cell membrane and gradually be absorbed by and integrated into the cells during sealing.

Current electroporation devices, however, have limitations. For example, many current electroporation devices have fixed cathodes and anodes, resulting in sub-optimal cell permeabilization. Moreover, many current electroporation devices can only perform electroporation within a small range of cell solution volumes. Further still, certain current electroporation devices are unable to perform electroporation with an accurate understanding of cell solution volumes and/or the position of fluids within an electroporation chamber, thus leaving the possibility of the device overfilling and consequently sub-optimal electroporation outcomes. Thus, there is a need to provide electroporation systems and methods that enable greater flexibility, accuracy, and efficacy in treating cells.

Disclosed herein are devices, systems, and methods for electroporation of cells. The disclosed devices, systems, and methods may be used with a wide range of cell volumes, and in some variations, the devices systems, and methods disclosed herein utilize multiple electroporation chambers, and/or sensors to assist with accuracy and efficacy.

As described throughout, the cell processing methods, devices, and systems may involve moving a cartridge containing a cell product between a plurality of instruments inside a workcell. One or more instruments may be configured to interface with a cartridge to perform cell processing steps. In some variations, a plurality of cell processing steps may be performed within a single cartridge. For example, a robotic arm may be configured to move a cartridge between instruments, each instrument configured to perform a different cell processing step when coupled to a corresponding module within the cartridge. The cartridge may comprise any number of modules, such as a bioreactor module, a counterflow centrifugal elutriation (CCE) module, a magnetic cell sorter module, an electroporation module, a sorting module (e.g., fluorescence activated cell sorting (FACS) module), a spinoculation module, an acoustic flow cell module, a microfluidic enrichment module, and/or combinations thereof, and the like. In some embodiments, the workcell may process two or more cartridges in parallel. For example, the workcell may comprise a plurality of bays, each bay configured to interface with a cartridge, such that multiple bays within the workcell may be in use at any given time. The cell processing systems described herein may reduce operator intervention and increase throughput by automating cartridge movement between instruments using a robot. However, in some embodiments, the cartridge may be moved between instruments manually. Moreover, the automated cell processing system may facilitate sterile liquid transfers between the cartridge and instruments or other components of the system such as a fluid connector (e.g., sterile liquid transfer port), reagent vault, a second cartridge, a sampling vessel e.g., sterile liquid transfer device, combinations thereof, and the like.

I. Cell Processing System

An illustrative cell processing system for use with the electroporation devices, systems, and methods is shown in FIG. 1A. Shown there is a block diagram of a cell processing system 100 comprising a workcell 110 and controller 120. The workcell 110 may comprise one or more of an instrument 112, a robot 116 (e.g., robotic arm), a reagent vault 118, a fluid connector 132, a sterilant source 129, a fluid source 136, a pump 138, and a sensor 140. A cartridge 114 and a sterile liquid transfer device 142, part of the cell processing system 100, may be used within the workcell 110. The controller 120 may comprise one or more of a processor 122, a memory 124, a communication device 126, an input device 128, and a display 130.

The workcell 110 may comprise a fully, or at least partially, enclosed housing inside which one or more cell processing steps are performed in a fully, or at least partially, automated process. In some variations, the workcell may be an open system lacking an enclosure, which may be configured for use in a clean room, a biosafety cabinet, or other sterile location. The cartridge 114 may be moved using the robot 116 to reduce manual labor in the cell processing steps, and sterile liquid transfers into and out of the cartridge may also be performed in a fully or partially automated process. For example, one or more fluids may be stored in a sterile liquid transfer device 142. In some variations, the sterile liquid transfer device is a portable consumable that may be moved within the system 100. The sterile liquid transfer devices and fluid connectors described herein may help enable the transfer of fluids in an automated, sterile, and metered manner for automating cell therapy manufacturing.

In some variations, the robot 116 is configured to move cartridges 114 between different instruments to perform a predetermined sequence of cell processing steps. In this way, multiple cartridges 114 may be processed in parallel, as different steps of the cell processing sequence may be performed at the same time on different cartridges.

A fluid connector 132 may be coupled between two or more cartridges 114 to transfer a cell product and/or fluid between the cartridges 114. Furthermore, a fluid connector 132 may be coupled between any set of fluid-carrying components of the system 100 (e.g., cartridge 114, reagent vault 118, fluid source 136, sterile liquid transfer device 142, fluid conduit, container, vessel, etc.). For example, a first fluid connector may be coupled between a first cartridge and a sterile liquid transfer device, and a second fluid connector may be coupled between the sterile liquid transfer device and a second cartridge.

Figure 1B:
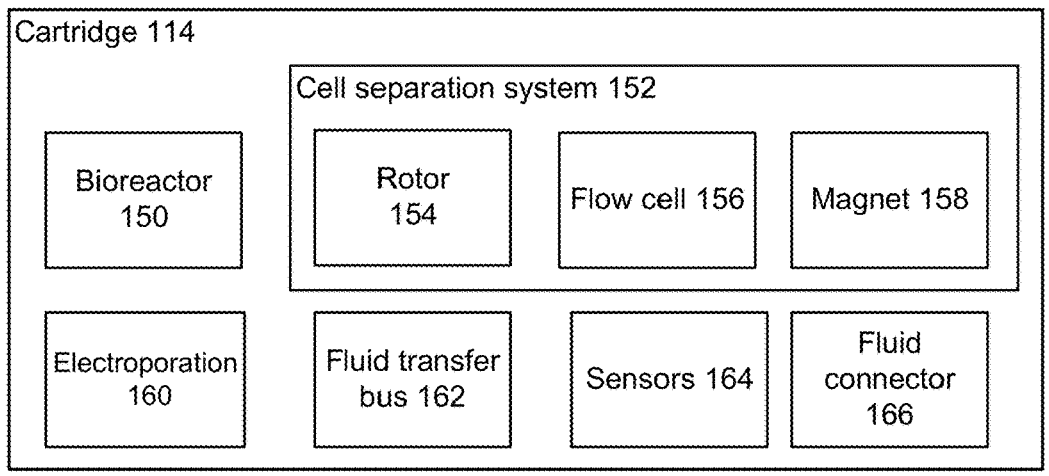
FIG. 1B is a block diagram of an illustrative variation of a cartridge.

As illustrated in FIG. 1B, a cartridge 114 may comprise one or more of a bioreactor 150, a cell separation system 152, an electroporation module 160, a fluid transfer bus 162, a sensor 164, and a fluid connector 166, as described in more detail herein. A cell separation system 152 may comprise one or more of a rotor 154, flow cell 156, and magnet 158. In some embodiments, the magnet 158 may comprise one or more magnets and/or magnet arrays. For example, the cell separation system 152 may comprise a first magnet configured to magnetically rotate a rotor 154 and a second magnet (e.g., magnet array) configured to magnetically separate cells in flow cell 156.

Any suitable cell processing may be performed using the systems and devices described herein, and may include steps such as growing, enriching, selecting, sorting, expanding, activating, transducing, electroporating, washing, and the like. In some variations, a method of processing a solution containing a cell product includes the steps of digesting tissue using an enzyme reagent to release a select cell population into solution, enriching cells using a CCE instrument, washing cells using the CCE instrument, selecting cells in the solution using a selection instrument, sorting cells in the solution using a sorting instrument, differentiating or expanding the cells in a bioreactor, activating cells using an activating reagent, electroporating cells, transducing cells using a vector, and finishing a cell product.

Figure 2A:
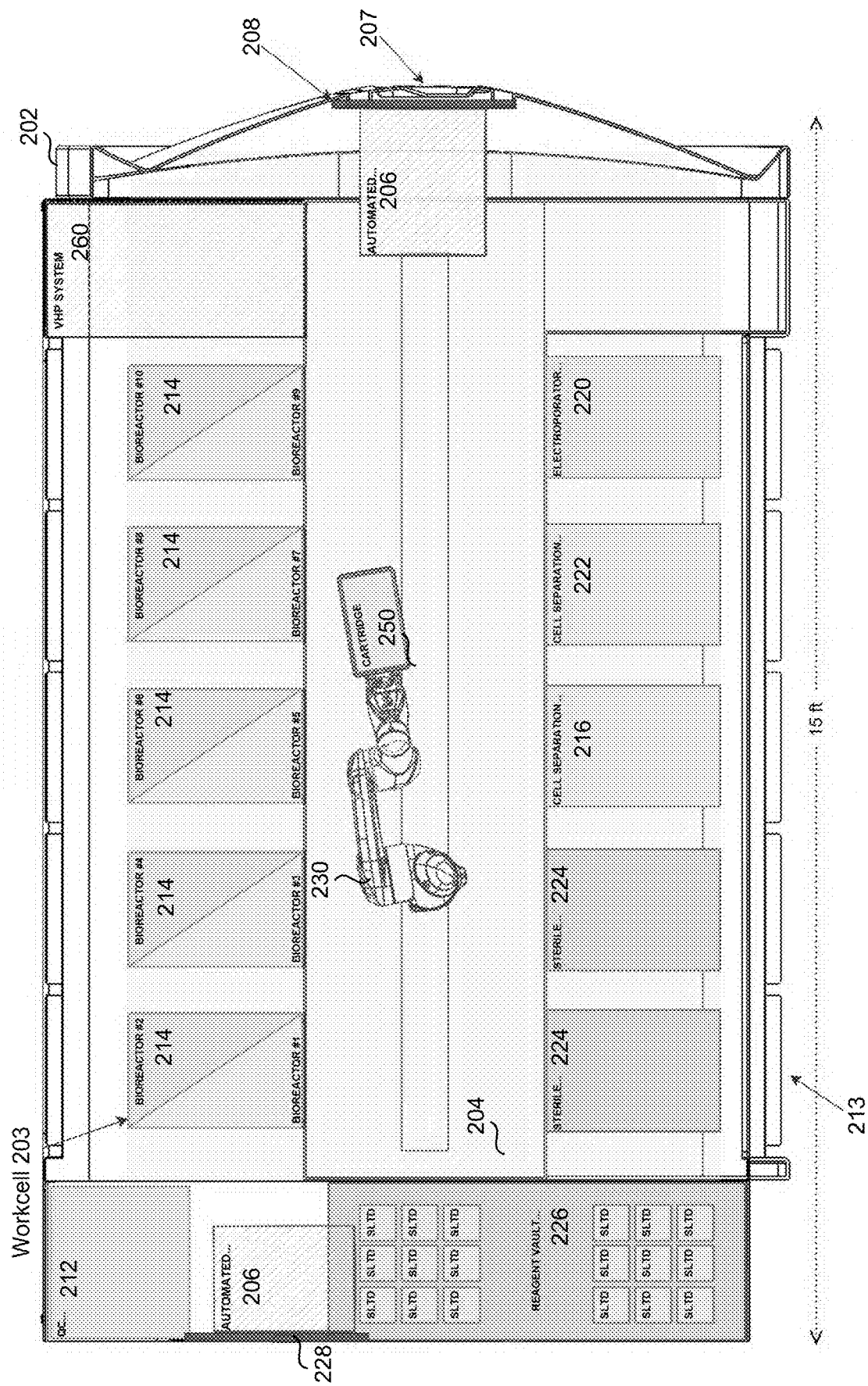
FIG. 2A is a block diagram of an illustrative variation of a cell processing system.
Figure 2B:
FIG. 2B is a perspective view of an illustrative variation of a workcell of a cell processing system.
Figure 2C:
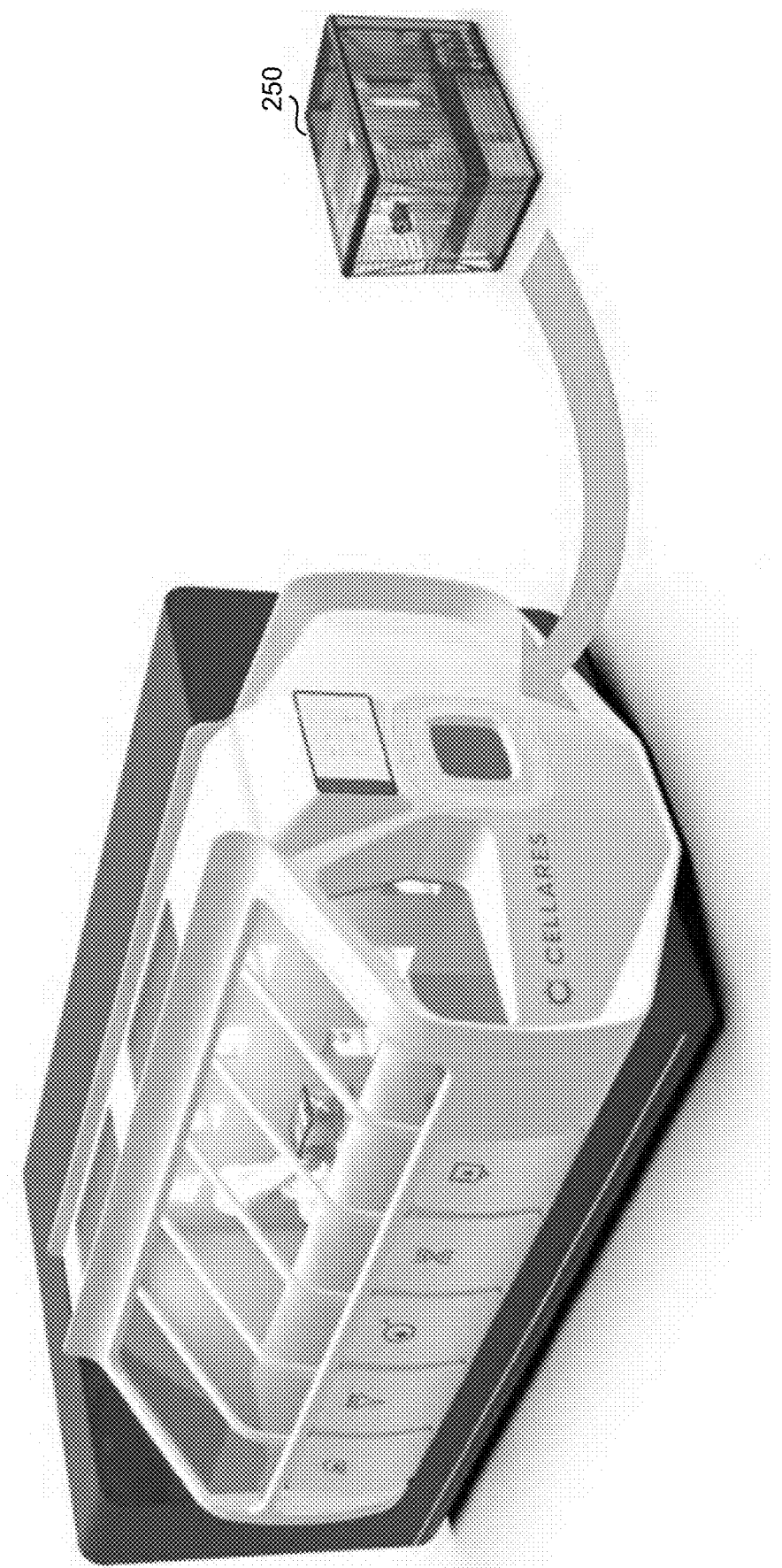
FIG. 2C is a perspective view of an illustrative variation of a workcell and cartridge of a cell processing system.

FIG. 2A shows an illustrative cell processing system for use with the devices, systems, and methods described herein. Shown there is workcell 203. The workcell may be divided into an interior zone 204 with a feedthrough 206 access, and quality control (QC) instrumentation 212. An air filtration inlet (not shown) may provide high-efficiency particulate air (HEPA) filtration to provide ISO7 or better air quality in the interior zone 204. This air filtration may maintain sterile cell processing in an ISO8 or ISO9 manufacturing environment. The workcell 203 may also have an air filter on the air outlet to preserve the ISO rating of the room. Similar to the workcell described above in reference to FIG. 1A, the workcell 203 may further comprise, inside the interior zone 104, a bioreactor instrument 214, a cell selection instrument 216 (e.g., magnetic separation instrument), an electroporation instrument 220, a counterflow centrifugation elutriation (CCE) instrument 222, a sterile liquid transfer instrument 224 (e.g., fluid connector), a reagent vault 226, and a sterilization system 260. The reagent vault 226 may be accessible by a user through a sample pickup port 228. A robot 230 (e.g., support arm, robotic arm) may be configured to move one or more cartridges 250 (e.g., consumables) from any instrument to any other instrument and/or move one or more cartridges 250 to and from a reagent vault. In some embodiments, the workcell 203 may comprise one or more moveable barriers 213 (e.g., access, door) configured to facilitate access to one or more of the instruments in the workcell 203. FIG. 2B is a perspective view of a workcell 205 of a cell processing system. FIG. 2C is a perspective view of a cell processing system depicting a cartridge 250 introduced into a workcell 205. A plurality of cartridges may be inserted into the workcell 205 and undergo one or more cell processing operations in parallel.

Figure 2D:
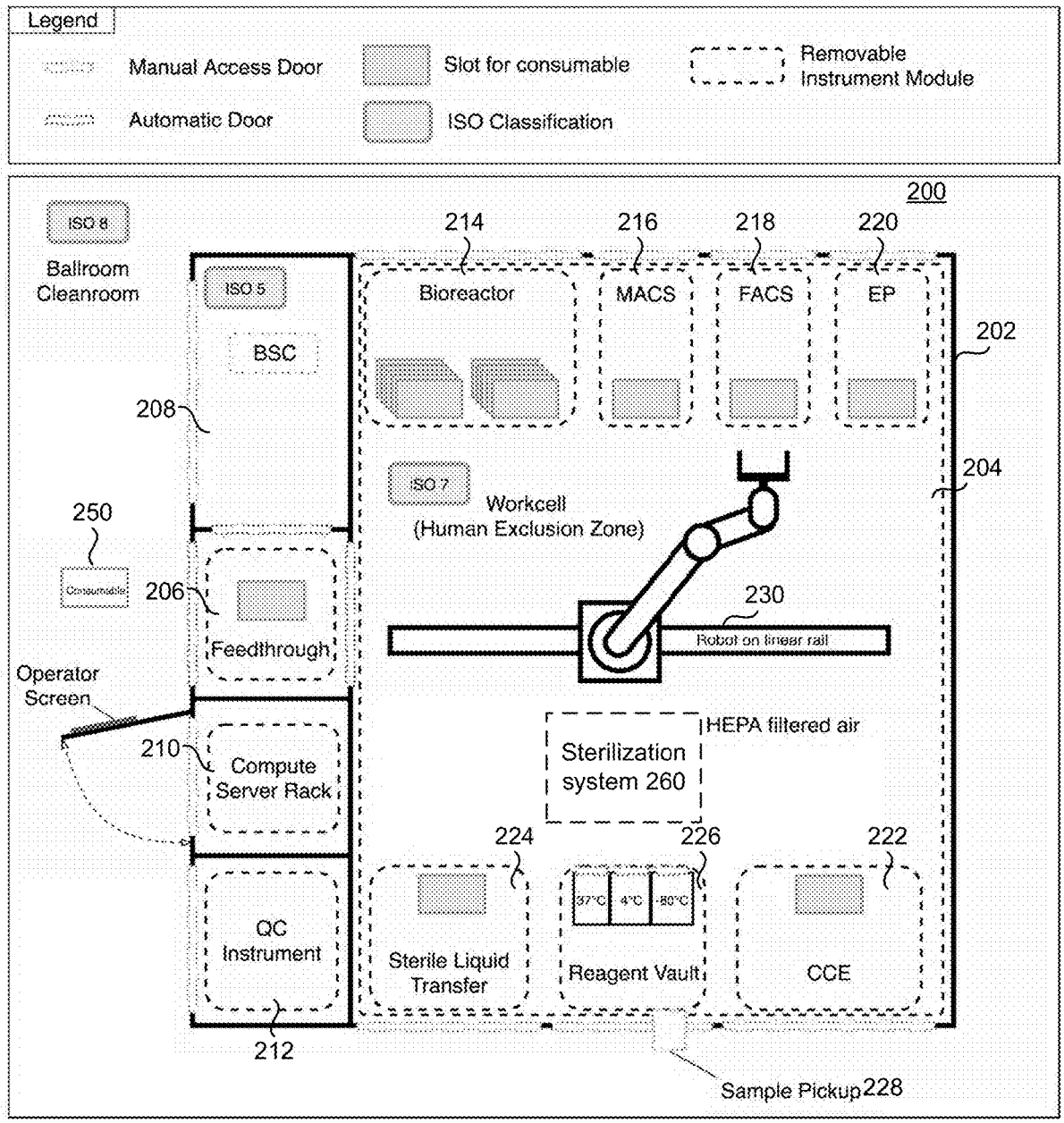
FIG. 2D is a block diagram of an illustrative variation of a cell processing system.

FIG. 2D is a schematic illustration of an embodiment of a workcell 200. Workcell 200 may comprise an enclosure 202 having four walls, a base, and a roof. The workcell may be divided into an interior zone 204 with a feedthrough 206 access, a biosafety cabinet (BSC) 208, compute server rack 210 (e.g., controller 120), and quality control (QC) instrumentation 212. An air filtration inlet (not shown) may provide high-efficiency particulate air (HEPA) filtration to provide ISO7 or better air quality in the interior zone 204. The workcell may also have an air filter on the air outlet to preserve the ISO rating of the room. As with the workcells described above, workcell 200 may further comprise, inside the interior zone 204, an instrument 211 (e.g., disposed in a universal instrument bay), a bioreactor instrument 214, a cell selection instrument 216 (e.g., magnetic separation instrument, cell selection system), a cell sorting instrument 218 (e.g., FACS), an electroporation instrument 220, and a counterflow centrifugation elutriation (CCE) instrument 222, a sterile liquid transfer instrument 224 (e.g., fluid connector), a reagent vault 226, and a sterilization system 260 comprising one or more of a sterilant source, fluid source, and a pump. The reagent vault 226 may be accessible by a user through a sample pickup port 228. A robot 230 (e.g., support arm, robotic arm) may be configured to move one or more cartridges 250 from any instrument to any other instrument or reagent vault.

In some embodiments, a human operator may load one or more cartridges 250 into the feedthrough 206. The cartridges 250 may be pre-sterilized, or the feedthrough 206 may sterilize the cartridge 250 using ultraviolet radiation (UV), or chemical sterilizing agents provided as a spray or wash. The feedthrough 206 chamber may optionally be configured to automatically spray, wash, irradiate, or otherwise treat cartridges (e.g., with ethanol and/or isopropyl alcohol solutions) to maintain sterility of the interior zone 204 (e.g., ISO 7 or better) or the biosafety cabinet 208 (e.g., ISO 5 or better). The cartridge 250 may be passed to the biosafety cabinet 206, where input cell product is provided and loaded to the cartridge using a sterile liquid transfer instrument 224 (e.g., fluid connector) into the cartridge 250. The user may then move the cartridge 250 back to the feedthrough 206 and initiate automated processing using a computer processor in the computer server rack 210 (e.g., controller 120). The robot 230 may be configured to move the cartridge 250 in a predefined sequence to a plurality of instruments and stations, with the components of the workcell 200 being controlled by the computer processor of the computer server rack 210.

Other suitable cell processing systems and aspects thereof are provided e.g., in U.S. patent application Ser. No. 17/198,134, published as U.S. Patent Publication No. 2021/0283565, which is incorporated by reference herein.

A. Workcell i. Robot

Generally, a robot of the workcell may comprise any mechanical device capable of moving a cartridge from one location to another location within the workcell. For example, the robot may comprise a mechanical manipulator (e.g., an arm) in a fixed location, or attached to a linear rail, or a 2- or 3-dimensional rail system. While shown in some of the figures as being fixed in place or with respect to a rail system, the robot need not be so. For example, in some variations, the robot comprises a wheeled device. Any number of robots may be used within the workcells described herein. For example, in some embodiments, the workcell comprises two or more robots of the same or different type (e.g., two robotic arms each independently configured for moving cartridges between instruments). The robot may also comprise an end effector for precise handling of different cartridges or barcode scanning or radio-frequency identification tag (RFID) reading. The robots for use with the cell processing systems described herein are capable of moving cartridges between slots or bays in the workcell so that the modules within the cartridge can couple to corresponding instruments within the workcell to perform different cell processing steps.

ii. Controller

In embodiments, a cell processing system 100 may comprise a controller 120 (e.g., computing device) comprising one or more of a processor 122, memory 124, communication device, 126, input device 128, and display 130. The controller 120 may be configured to control (e.g., operate) the workcell 110. The controller 120 may comprise a plurality of devices. For example, the workcell 110 may enclose one or more components of the controller 120 (e.g., processor 122, memory 124, communication device 126) while one or more components of the controller 120 may be provided remotely to the workcell 110 (e.g., input device 128, display 130).

iii. Processor

The processor (e.g., processor 122) described here may process data and/or other signals to control one or more components of the system. The processor may be configured to receive, process, compile, compute, store, access, read, write, and/or transmit data and/or other signals. Additionally, or alternatively, the processor may be configured to control one or more components of a device (e.g., console, touchscreen, personal computer, laptop, tablet, server).

In some embodiments, the processor may be configured to access or receive data and/or other signals from one or more of workcell 110, server, controller 120, and a storage medium (e.g., memory, flash drive, memory card, database). In some embodiments, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including structured text, typescript, C, C++, C#, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

iv. Memory

The cell processing systems and devices described here may include a memory (e.g., memory 124) configured to store data and/or information. In some embodiments, the memory may include one or more of a random-access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory may store instructions to cause the processor to execute modules, processes, and/or functions associated with the device, such as image processing, image display, sensor data, data and/or signal transmission, data and/or signal reception, and/or communication. Some embodiments described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The computer code (also may be referred to as code or algorithm) may be those designed and constructed for the specific purpose or purposes. In some embodiments, the memory may be configured to store any received data and/or data generated by the controller and/or workcell. In some embodiments, the memory may be configured to store data temporarily or permanently.

v. Input Device

In some embodiments, an input device 128, for example, may comprise or be coupled to a display. The input device may be any suitable device that is capable of receiving input from a user, for example, a keyboard, buttons, touch screen, etc. The input device may include at least one switch configured to generate a user input. For example, an input device may include a touch surface for a user to provide input (e.g., finger contact to the touch surface) corresponding to a user input. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In embodiments of an input device including at least one switch, a switch may have, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a user input. A microphone may receive audio data and recognize a user voice as a user input.

In some embodiments, the cell processing system may optionally include one or more output devices in addition to the display, such as, for example, an audio device and haptic device. An audio device may audibly output any system data, alarms, and/or notifications. For example, the audio device may output an audible alarm when a malfunction is detected. In some embodiments, an audio device may include at least one of a speaker, a piezoelectric audio device, a magnetostrictive speaker, and/or a digital speaker. In some embodiments, a user may communicate with other users using the audio device and a communication channel. For example, a user may form an audio communication channel (e.g., VoIP call).

Additionally, or alternatively, the system may include a haptic device configured to provide additional sensory output (e.g., force feedback) to the user. For example, a haptic device may generate a tactile response (e.g., vibration) to confirm user input to an input device (e.g., touch surface). As another example, haptic feedback may notify that user input is overridden by the processor.

vi. Communication Device

In some embodiments, the controller may include a communication device (e.g., communication device 126) configured to communicate with another controller and one or more databases. The communication device may be configured to connect the controller to another system (e.g., Internet, remote server, database, workcell) by wired or wireless connection. In some embodiments, the system may be in communication with other devices via one or more wired and/or wireless networks. In some embodiments, the communication device may include a radiofrequency receiver, transmitter, and/or optical (e.g., infrared) receiver and transmitter configured to communicate with one or more devices and/or networks. The communication device may communicate by wires and/or wirelessly.

vii. Display

Image data may be output on a display e.g., display 130) of a cell processing system. In some embodiments, a display may include at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

viii. Graphical User Interface

In some embodiments, as indicated above, a GUI may be configured for designing a process and monitoring a product. For example, the GUI may be a process design home page. The GUI may indicate that no processes have been selected or loaded. A create icon (e.g., "Create a Process") may be selectable for a user to begin a process design process. In some embodiments, one or more of the GUIs described herein may include a search bar.

B. Cartridge

The cell processing systems described herein may comprise one or more cartridges having one or more modules configured to interface with one or more instruments within the workcell.

Various materials may be used to construct the cartridge and the cartridge housing, including metal, plastic, rubber, and/or glass, or combinations thereof. The cartridge, its components, and its housing may be molded, machined, extruded, 3D printed, or any combination thereof. The cartridge may contain components that are commercially available (e.g., tubing, valves, fittings)—these components may be attached or integrated with custom components or devices. The housing of the cartridge may constitute an additional layer of enclosure that further protects the sterility of the cell product.

In some embodiments, the modules may be integrated in a fixed configuration within the cartridge. Additionally, or alternatively, the modules may be configurable or moveable within the cartridge, permitting various formats of cartridges to be assembled. For example, the cartridge can be a single, closed unit with fixed components for each module, or the cartridge may contain configurable modules coupled by configurable fluidic, mechanical, optical, and electrical connections. In some variations, one or more sub-cartridges, each containing a set of modules, may be used to perform various cell processing workflows. The modules may each be provided in a distinct housing or may be integrated into a cartridge or sub-cartridge with other modules. The disclosure generally shows modules as distinct groups of components for the sake of simplicity, but it should be noted that these modules may be arranged in any suitable configuration. For example, the components for different modules may be interspersed with each other such that each module is defined by the set of connected components that collectively perform a predetermined function. However, the components of each module may or may not be physically grouped within the cartridge. In some embodiments, multiple cartridges may be used to process a single cell product through transfer of the cell product from one cartridge to another cartridge of the same or different type and/or by splitting cell product into more cartridges and/or pooling multiple cell products into fewer cartridges.

Generally, each of the instruments within the workcell interfaces with its respective module or modules on the cartridge. For example, when a cartridge has an electroporation module, it is moved by the robot to the electroporation instrument within the workcell to perform electroporation on the cells within the cartridge. One advantage of such split module/instrument designs is that expensive components (e.g., motors, sensors, heaters, lasers, etc.) may be retained in the instruments of the system while less expensive components reside in the cartridge, which is typically disposable and configured for single-use. The use of disposable cartridges may eliminate the need to sterilize cartridges between use. Furthermore, having multiple instruments within the workcell further helps allow for the parallel utilization of those instruments when multiple cartridges are used within the workcell. In contrast, most conventional semi-automated instruments have instrument components that sit idle and are incapable of simultaneous parallel use.

Additional aspects of suitable cartridges are provided e.g., in U.S. patent application Ser. No. 17/198,134, published as U.S. Patent Publication No. 2021/0283565, which is incorporated by reference herein.

C. Electroporation System

As described above, one of the cell processing steps that may be performed is electroporation. In variations, where electroporation is performed, the cartridge comprises an electroporation module and the workcell comprises a corresponding electroporation instrument. The electroporation module within the cartridge may comprise one or more electroporation chambers, and the electroporation instrument may be configured to apply electroporation energy to the one or more electroporation chambers to electroporate cells therein.

The energy may be applied to the electroporation chambers simultaneously or sequentially. To this end, the electroporation instrument may be configured to deliver electrical energy to the electroporation chamber. The amount of energy supplied to the electroporation chambers may be predetermined or may be based on the volume of cell solution within the electroporation chamber.

FIGS. 3A-3F provide schematic and exemplary illustrations of electroporation chambers of the present disclosure.

Figure 3A:
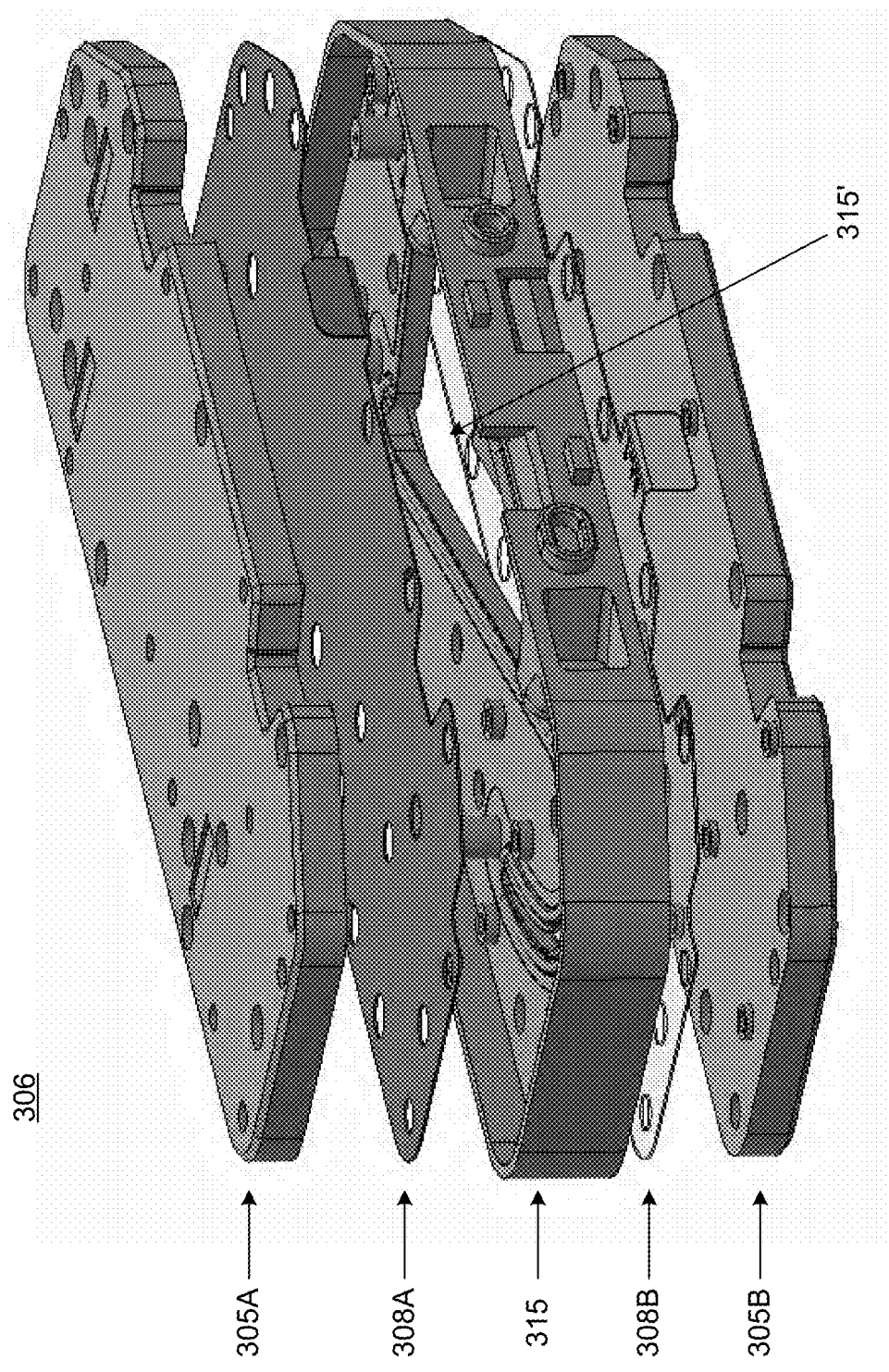
FIG. 3A is a rendering of an exploded view of an illustrative electroporation chamber of a cartridge.

FIG. 3A provides an exploded view of an exemplary electroporation chamber 306. The electroporation chamber 306 may comprise a first housing 305A, a first electrode 308A, an electroporation cell 315, a second electrode 308B, and a second housing 305B. The first housing 305A and second housing 305B may sandwich, surround, envelope, or otherwise contain the first electrode 308A, electroporation cell 315, and second electrode 308B. As illustrated in FIG. 3A, the first electrode 308A may form a layer between the first housing 305A and electroporation cell 315. The second electrode 308B may form a layer between the second housing 305B and electroporation cell 315. The first electrode 308A may be coupled to a first surface of the electroporation cell 315. The second electrode 308B may be coupled to a second surface of the electroporation cell 315. A distance between the first surface of the electroporation cell 315 and the second surface of the electroporation cell 315, together with an opening 315' of the electroporation cell 315, define a fluid conduit of the electroporation chamber 306. The fluid conduit will be described in further detail below. The first electrode 308A and the second electrode 308B may have at least one alignment feature that corresponds to at least one alignment feature of the electroporation cell 315. For example, the at least one alignment feature may be an orifice, hole, protrusion, indent, or any other surface feature. The first electrode 308A and the second electrode 308B may be coupled to the electroporation cell 315 in any suitable manner such as, for example, glue, screws, adhesive, friction, or other similar fastening devices or mechanisms.

The first electrode 308A, the second electrode 308B, and the electroporation cell 315 may be aligned relative to each other using the at least one alignment feature and subsequently compressed to form a water-tight seal around the perimeter of the combined assembly. The coupling of the first and second housings 305A, 305B around the first and second electrodes 308A, 308B and electroporation cell 315 may be fluidically sealed. The fluid seal may be achieved via an adhesive, a polymer, a welding procedure, a coupling tab, an interlocking digit, or any other similar mechanism. The fluid seal may prevent substantially any cell solution from leaking between the layers to the external environment. The fluid seal may prevent substantially any substance in the external environment from seeping into the electroporation chamber and/or electroporation system.

Figure 3B:
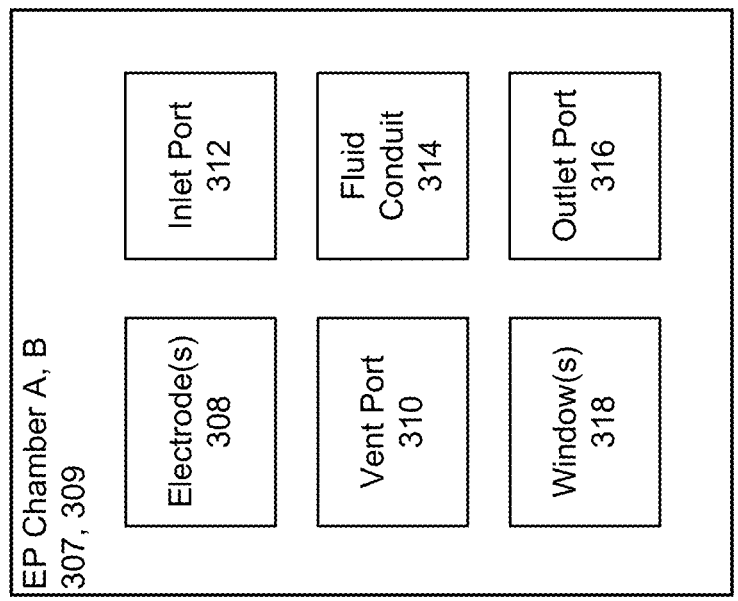
FIG. 3B is a schematic diagram of an illustrative electroporation chamber of a cartridge.

FIG. 3B is a schematic diagram of a system including one or more electroporation chambers, such as electroporation chamber A 307 and electroporation chamber B 309. For simplicity, FIGS. 3B-3F will be described with reference to a single electroporation chamber (e.g., chamber A 307), where appropriate. Chamber A 307 may comprise at least one electrode 308. For example, and with reference to FIG. 3A, chamber A 307 may comprise a first electrode 308A and a second electrode 308B, which may be electrically conductive and configured to generate an electric field therebetween. The electric field may be generated to induce membrane permeabilization of cells within a fluid conduit 314 of chamber A 307, as will be described below.

The electric field may be determined by the applied voltage (V) and distance (d) between the electrodes 308A, 308B. For example, the electrical field (E) may be calculated by the equation $E=V/d$. In some variations, the distance between the first electrode 308A and the second electrode 308B may be between about 0.5 mm and about 5 mm. For instance, the distance between the first electrode 308A and the second electrode 308B may be at least about 0.5 mm, at least about 1 mm, at least about 1.5 mm, at least about 2 mm, at least about 2.5 mm, at least about 3 mm, at least about 3.5 mm, at least about 4 mm, and/or at least about 4.5 mm. In some embodiments, the distance between the electrodes 308A, 308B may be fixed, e.g., at $d=2$ mm. The applied voltage may be determined by the type of cell to be treated. For example, pores of T-cells may open in an effective electric field of about 1 to 3 kV/cm. If an effective electric field of 1 kV/cm is desired, the required voltage may be 200 V. If an effective electric field of 3 kV/cm is desired, the required voltage may be 600 V. Generally, the effective electric field between at least two electrodes in at least one electroporation chamber may be at least 100 V/cm, at least 200 V/cm, at least 300 V/cm, at least 400 V/cm, at least 500 V/cm, at least 600 V/cm, at least 700 V/cm, at least 800 V/cm, at least 900 V/cm, at least 1 kV/cm, at least 2 kV/cm, at least 3 kV/cm, at least 4 kV/cm, and at least 5 kV/cm.

Chamber A 307 may further comprise a fluid conduit 314. During an electroporation process, the fluid conduit 314 may be configured to receive a cell solution volume up to and including 2.5 mL. For example, the fluid conduit 314 may be capable of containing a volume of at least 0.5 mL, at least 1 mL, at least 1.5 mL, at least 2 mL, at least 3 mL, at least 3.5 mL, at least 4 mL, at least 4.5 mL, and at least 5 mL. In some variations, the fluid conduit 314 may be configured to contain between about 1.5 mL to about 2.0 mL of fluid. To this end, a volume of the fluid conduit 314 is based on a shape of an opening (opening "O" in FIG. 3A) within the electroporation cell 315 and on a depth of the opening, the depth defining a distance separating the first electrode 308A from the second electrode 308B when the electroporation chamber is assembled. The fluid conduit 314 may be configured to contain a mixture of gases and liquids.

The chamber A 307 may further comprise an inlet port 312, an outlet port 316, and a vent port 310. At least one of the inlet port 312, the outlet port 316, and the vent port 310 may be configured to control and/or permit fluid (e.g., a gas, a liquid, or a mixture thereof) flow into and/or out of the fluid conduit 314. For example, each port may have a closed configuration and an open configuration. In the closed configuration, each of the plurality of ports may prevent flow of fluid therethrough. In the open configuration, each of the plurality of ports may allow flow of fluid therethrough. In some embodiments, each of the plurality of ports may have a partially open configuration. For example, the partially open configuration may allow fluid flow at a reduced flow rate as compared to the open configuration. Each of the plurality of ports may cause a pressure drop in the fluid flowing therethrough. The pressure drop associated with one port may be different than the pressure drop associated with any other port. It should also be noted that the ports need not be configured to have the same configuration at the same time. Some of the ports may be open, while others are closed, or partially open.

Figure 3C:
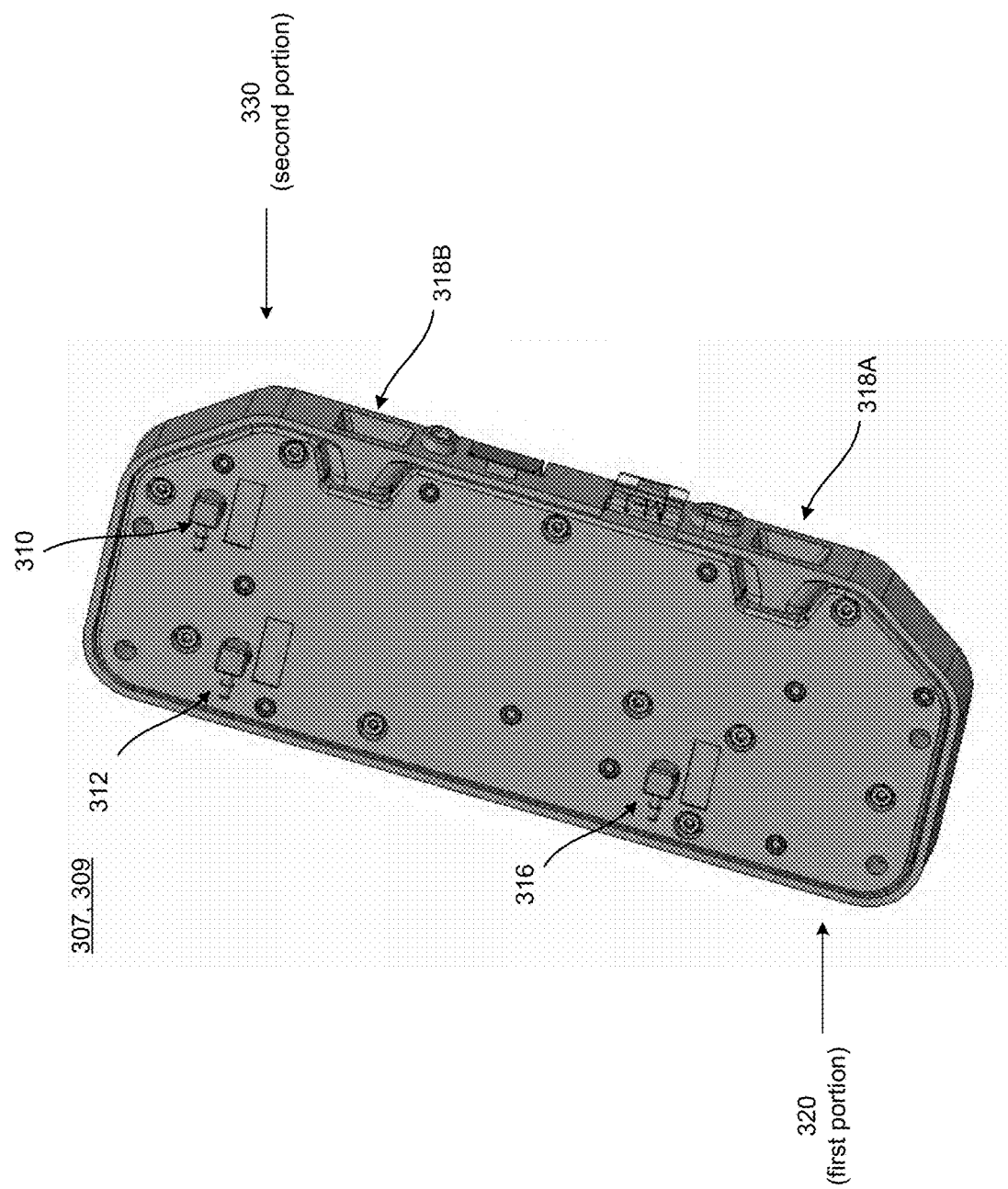
FIG. 3C is a rendering of a perspective view of an illustrative electroporation chamber of a cartridge.

FIG. 3C provides an illustrative depiction of an electroporation chamber that may be used with the systems, devices, and methods described herein. The electroporation chamber may be an electroporation chamber A 307 and/or an electroporation chamber B 309. Electroporation chambers 307, 309 may comprise a first portion 320 and a second portion 330. The first portion 320 may comprise an outlet port 316 and a first window 318A. The second portion may comprise an inlet port 312, a vent port 310, and a second window 318B.

In some embodiments, there may be a first window through a side wall providing a view into the first portion of the electroporation chambers 307, 309. There may also be a second window providing a view into the second portion of the electroporation chambers 307, 309. The first and second windows may advantageously provide visibility into respective portions of the fluid conduit 314. In some embodiments, there may be three or more windows. For example, a third window may be arranged proximate the inlet port 312. In some embodiments, a window may be proximate any of the plurality of ports. In some embodiments, the windows 318A, 318B may comprise a transparent material such as, for example, glass, polymers, or combinations thereof. The window material may comprise a flexible, durable material that may withstand one or more of vibrations, deflections, and twisting without cracking or shattering.

In some embodiments, an electroporation instrument may comprise at least one sensor corresponding to one of the windows 318A, 318B. For example, a first sensor may be located proximate the first window 318A, and a second sensor may be located proximate the second window 318B. The sensors may be external to an electroporation chamber and located within 1 in., 2 in., 3 in., 4 in., 5 in., or 6 in. of the window. In some embodiments, the sensors have a direct line of sight into the fluid conduit 314 of the electroporation chamber 307, 309. The at least one sensor may be configured to detect the presence or absence of fluid within the fluid conduit 314. The at least one sensor may be any suitable sensor, for example, an optical sensor, pressure sensor, infrared sensor, a capacitance sensor, or any combination thereof.

In some embodiments, at least one sensor may be proximate to at least one of the outlet port 316, the inlet port 312, and the vent port 310. The at least one sensor may be proximal to other components within the electroporation system as well, such as, for example, a fluid pump and a fluid pipe. The at least one sensor may be configured to detect the fill state of the fluid conduit 314. For example, the at least one sensor may detect if the fluid conduit 314 is substantially empty, or whether the fluid conduit 314 contains the target volume of fluid. In some embodiments, the at least one sensor may detect if the fluid conduit 314 contains a volume of fluid in excess of the target volume. The at least one sensor may also detect if the fluid is flowing into or out of the fluid conduit 314 through at least one the inlet port 312, the outlet port 316, and the vent port 310. The at least one sensor may detect if there is a substantially zero flow rate into or out of the fluid conduit 314.

The inlet port 312, the outlet port 316, and the vent port 310 may extend or protrude from the electroporation cell 315. In some embodiments, the inlet port 312, the outlet port 316, and the vent port 310 extend or protrude from the electroporation cell 315 through at least one of the first electrode 308A and first housing 305A and/or the second electrode 308B and the second housing 305B. This permits the windows 318A, 318B to be suitable arranged at any location around a perimeter of the electroporation chamber. In some embodiments, any of the plurality of ports may protrude through any other wall or surface of the electroporation chamber. For example, at least one of the plurality of ports may extend from the electroporation cell 315 through a side wall of the electroporation chamber and may not extend through any one of the electrodes. In some embodiments, the location of the plurality of ports may help minimize at least one dimension of the electroporation chamber.

Figure 3D:
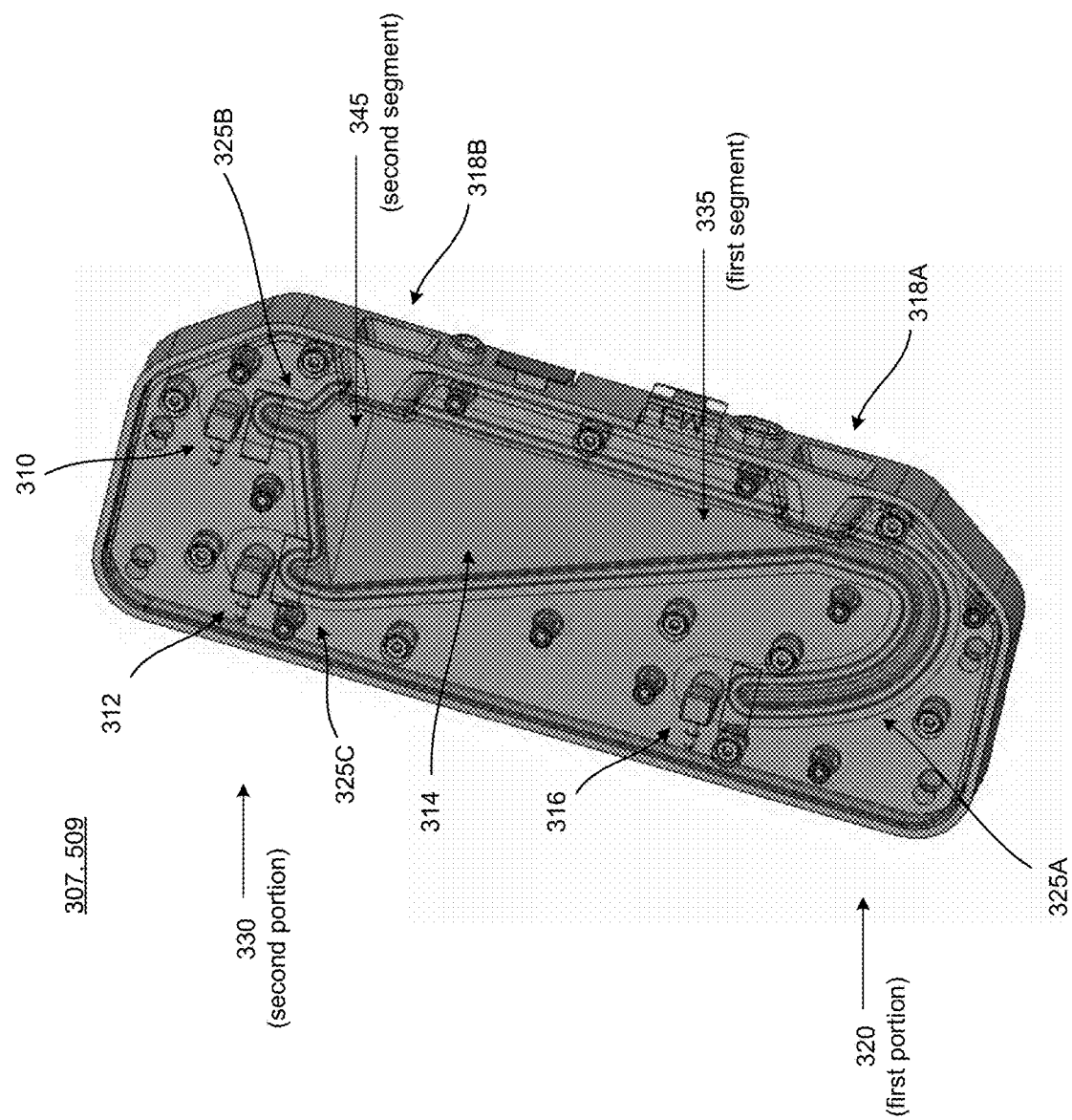
FIG. 3D is a rendering of an aspect of an illustrative electroporation chamber of a cartridge.

FIGS. 3D-3F provide additional illustrative views of electroporation chamber 307, 309. The electroporation chamber 307, 309 may comprise a first portion 320. The first portion 320 may comprise at least one auxiliary channel such as, for example, a first auxiliary channel 325A. The first auxiliary channel 325A may fluidically connect an outlet port 316 to a fluid conduit 314. The first portion 320 may further comprise the first window 318A, which may be fluidically connected to at least one of the auxiliary channel 325A and fluid conduit 314. A first window 318A may be arranged on a side wall of the electroporation chamber 307, 309 and proximate the first auxiliary channel 325A coupled to the outlet port 316. The fluid conduit 314 may comprise a cavity configured to receive a fluid such as, for example, a cell solution. The fluid conduit 314 may comprise a first segment 335 and a second segment 345. In some embodiments, the first segment 335 of the fluid conduit 314 may be proximate a first portion 320 of the electroporation chamber 307. In some embodiments, the second segment 345 of the fluid conduit 314 may be proximate a second portion 330 of the electroporation chamber 307.

The second portion 330 may comprise at least one auxiliary channel. The second portion 330 may comprise a second auxiliary channel 325B and a third auxiliary channel 325C. The second auxiliary channel 325B may fluidically connect the inlet port 312 to the fluid conduit 314. The third auxiliary channel 325C may fluidically connect the vent port 310 to the fluid conduit 314. As with the first auxiliary channel 325A, the second auxiliary channel 325B and the third auxiliary channel 325C may each have windows proximate thereto. A second viewing window 318B may be positioned proximate the second auxiliary channel 325B coupled to the vent port 310. In some embodiments, a third window may be positioned proximate the third auxiliary channel 325C coupled to the inlet port 312.

In some embodiments, the fluid conduit 314 may be in fluid communication with each of the plurality of ports 310, 312, 316 via the auxiliary channels 325A, 325B, 325C extending therefrom. The auxiliary channels 325A, 325B, 325C may have any suitable cross-sectional shape such as, for example, circular, square, rectangular, triangular, or combinations thereof. In some embodiments, the fluid conduit 314 may have a triangular cross-section along an axis defined from the first portion 320 of the electroporation chamber 307, 309 to the second portion 330 of the electroporation chamber 307, 309. In some embodiments, there may be surface features on the inner surface of the auxiliary channels 325A, 325B, 325C. The auxiliary channel 325A in fluid communication with the outlet port 316 may be curvilinear. In some embodiments, the first window 318A is proximate the at least one curvilinear auxiliary channel. In some embodiments, the first window 318A may be proximate a base of the curvilinear auxiliary channel. In some embodiments, the second window 318B may be proximate the auxiliary channel 525B in fluid communication with the vent port 310. In some embodiments, the second window 318B may be proximate a base of the auxiliary channel 525B in fluid communication with the vent port 310. The inlet port 312, outlet port 316, and vent port 310 may each be configured to direct fluid flow. For example, the inlet port 312 may be configured to receive flow from an external source and direct the fluid into the fluid conduit 314 via the auxiliary channel 325C. The at least one sensor may be proximate at least one the auxiliary channels 325A, 325B, and 325C.

In some embodiments, the inlet port 312 may receive fluid from a fluid transfer bus of the cartridge. The outlet port 316 may be configured to receive fluid from the fluid conduit 314 and direct the fluid to an external component. In some embodiments, the outlet port 316 may be configured to direct fluid into a fluid pump apparatus or fluid transfer bus. The vent port 310 may be configured to release fluid from the fluid conduit 314 and/or purge the fluid. For example, the fluid released through and/or purged via the vent port 310 may be a gas or a liquid. The fluid within the fluid conduit 314 may be air, a byproduct of the electroporation process of a cell solution, or any other gas.

Figure 4A:
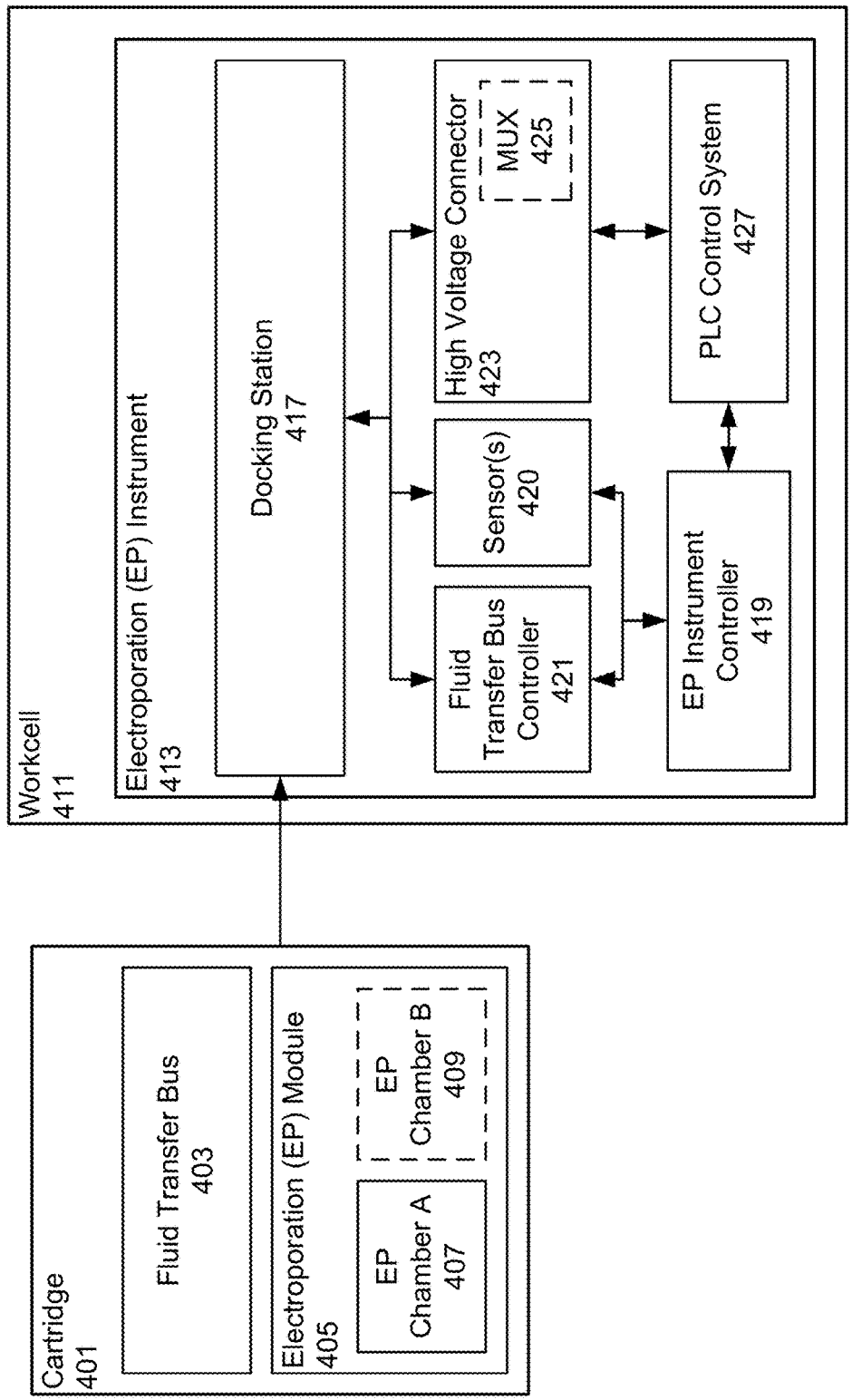
FIG. 4A is a schematic diagram of an illustrative variation of an electroporation system showing an electroporation instrument within a workcell and a corresponding electroporation module within a cartridge.

Turning now to FIG. 4A, a schematic diagram of an illustrative electroporation system 400, comprising at least one electroporation module 405 within at least one cartridge 401 and at least one electroporation instrument 413 within a workcell 411, is provided. The electroporation system 400 has at least one electroporation chamber (e.g., 407, 409) of an electroporation module 405 of a cartridge 401. The electroporation module 405 is configured to couple to the electroporation instrument 413 of the workcell 411 so that electroporation may be carried out. The electroporation module 405 may be operatively coupled to, or otherwise interface with, the module so that electrical energy may be delivered to the at least one electroporation chamber.

The at least one electroporation chamber of the electroporation module 405 may comprise a first electroporation chamber 307 ("EP Chamber A") and, optionally, a second electroporation chamber 409 ("EP Chamber B"). The electroporation chambers 407, 409 may be located adjacent to one another within the cartridge 401 but need not be. In some embodiments, the electroporation chambers 407, 409 may be separated from each other within the cartridge 401.

The cartridge 401 may comprise a fluid transfer bus 403 fluidically coupling the electroporation module 405 with the other modules of the cartridge 401. The fluid transfer bus 403 may be configured to transport, via tubing or piping, at least one type of fluid between modules of the cartridge 401. The fluid may be a liquid, a gas, or a mixture thereof. The fluid transported within the fluid transfer bus 403 may be a reagent, or a cell solution comprising any type of cells, including patient-derived cells or allogeneic cells.

The electroporation instrument 413 may comprise a docking station 417 configured to receive the cartridge 401. The docking station 417 may comprise a cavity comprising structural features corresponding to features on the cartridge 401. For example, the docking station may have at least one track that is configured to receive at least one rail, wheel, protrusion, indent, or similar feature on the cartridge 401. The cartridge 401 may be configured to slidably fit into docking station 417 of electroporation instrument 413. For example, the cavity may be sized to be slightly larger than the shape and size of the cartridge 401. The cartridge may rely on friction forces to be held within the docking station 417. In some embodiments, the cartridge may be held in place via at least one of magnets, latches, push rods, or similar features. The docking station may further comprise at least one electroporation feature (e.g., high voltage connector) on a surface of the cavity to interface with electrodes of the electroporation module 305 of the cartridge 401 when the cartridge 401 is within the docking station 417.

Electroporation instrument 413 may comprise a high voltage connector 423 and a programmable logic controller (PLC) control system 327. The PLC control system 327 may be electrically connected to the high voltage connector 423. The PLC control system 327 may send at least one of digital and analog signals to the high voltage connector 423. In some embodiments, the PLC control system 327 may send electrical signals to the high voltage connector 423.

The high voltage connector 423 may be electrically connected to the docking station 317. The high voltage connector 423 may connect to at least one surface feature of the docking station 317. In some embodiments, the high voltage connector 423 may electrically couple to at least one electrical lead or electrode on the docking station. In some embodiments, the high voltage connector 423 may contact features of the electroporation module 305 of the cartridge 401 via an electroporation feature on the surface of the cavity when the cartridge 401 is within the docking station 317.

In embodiments, the high voltage connector 423 further comprises a multiplexer (MUX) 425. The MUX 425 may be a mechanical multiplexer. For example, the MUX 425 may comprise mechanical switches that physically move in response to at least one input signal. The MUX 425 may be configured to adjust the output of the high voltage connector 423. For example, the MUX 425 may isolate the output of the high voltage connector 423 to a selected electroporation chamber, such as EP Chamber A 407 or EP Chamber B 409. In some embodiments, the MUX 425 may rapidly switch the outputs between the electroporation chambers. In some embodiments, the MUX 425 may select both electroporation chambers at the same time and thus provide electrical outputs to both EP Chamber A 407 and EP Chamber B 409, simultaneously.

The electroporation instrument 413 may further comprise an electroporation instrument controller 419 and a fluid transfer bus controller 421. The electroporation instrument controller 319 may control at least one function of the electroporation instrument 413. For example, the electroporation instrument controller 419 may control at least one of the fluid transfer bus controller 421, at least one sensor 420, or the programmable logic controller (PLC) control system 427 via at least one electrical signal. In some variations, the electroporation instrument controller 419 sends a signal to the fluid transfer bus controller 421 that starts or stops fluid flow from the fluid transfer bus to EP Chambers A and B (407 and 409). In some variations, the electroporation instrument controller 319 receives a signal from the fluid transfer bus controller 421 that indicates a status of the flow, or lack thereof, of fluid through the fluid transfer bus 403. The electroporation instrument controller 419 may send an electrical signal to the at least one sensor 420. For example, the electroporation instrument controller 419 may switch the state of the at least one sensor 420 from on to off, or vice versa. In some variations, the electroporation instrument controller 419 receives a signal from the at least sensor 420. For example, the at least one sensor 420 may provide continuous or discontinuous output signals to the electroporation instrument controller 419. In some embodiments, the output signal from the at least one sensor 420 may be one or more of a video stream, a picture, digital or analog electrical signals, pressure measurements, capacitance measurements, and combinations thereof.

The electroporation instrument controller 419 may send an electrical signal to the PLC control system 427, as well. For example, the electroporation instrument controller 419 may transmit a power input to the PLC control system 427 that may switch the state of the PLC control system 427 from on to off, or vice versa. In some embodiments, the power signal transmitted from the electroporation instrument controller 419 to the PLC control system 427 comprises a desired output voltage that should be supplied to the high voltage connector 423 and, thus, the electroporation module 405 of the cartridge 401. The desired output voltage may be preset, predetermined, or be dependent on one or more factors and determined in real-time using one or sensors. For example, the output voltage may be determined at least in part based upon the type of cells within a cell solution to be electroporated. The electroporation instrument controller 419 may receive a signal from the PLC control system 427. For example, the PLC control system may transmit one or more of a resistance value, a voltage value, and an on/off status to the electroporation instrument controller 419. The electroporation controller 419, PLC control system 427, fluid transfer bus controller 421, and sensor 420 may all be in electrical communication. It should be appreciated that data received from any one of the fluid transfer bus controller 421, the at least one sensor 420, and the PLC control system 427 may impact subsequent instructions generated by the electroporation instrument controller. For example, data received from the at least one sensor 420 may cause the electroporation instrument controller 419 to send an instruction to the fluid transfer bus controller 421 to cease fluid flow. In another example, data received from the at least one sensor 420 may cause the electroporation instrument controller 419 to send instructions to the PLC control system 427 to begin electroporation.

In some variations, the electroporation instrument controller 419 sends a signal to the fluid transfer bus controller 421 that, in turn, sends a signal to the docking station 417. For example, the fluid transfer bus controller 421 may send at least one signal to at least one feature of the docking station 417 that is configured to engage with the cartridge 401. For example, the fluid transfer bus controller 421 may turn on or off a locking mechanism within the docking station that is configured to hold the cartridge 401 within the docking station. The fluid transfer bus controller 421 may indicate the status of the docking station 417 and the cartridge 401. For example, the status may be an indication that the cartridge 401 is successfully engaged with the docking station 417. In another example, the status may be an indication that there is a fluid-tight seal between the fluid paths between system components.

The fluid transfer bus control 421 may control at least one function of the at least one fluid transfer bus 403 within the cartridge 401. For example, as introduced above, the fluid transfer bus control 421 may send a signal to start or stop flow within the fluid transfer bus 403. In embodiments, the fluid bus control 421 may send signals to multiple components on the cartridge 401. For example, the fluid transfer bus controller 421 may send a signal to a fluid pump fluidically coupled to the fluid transfer bus 403 of the cartridge 401 to begin fluid flow and also send a signal to an inlet port to open the inlet port. In embodiments, the fluid bus control 421 may send multiple signals to multiple components simultaneously.

Figure 4B:
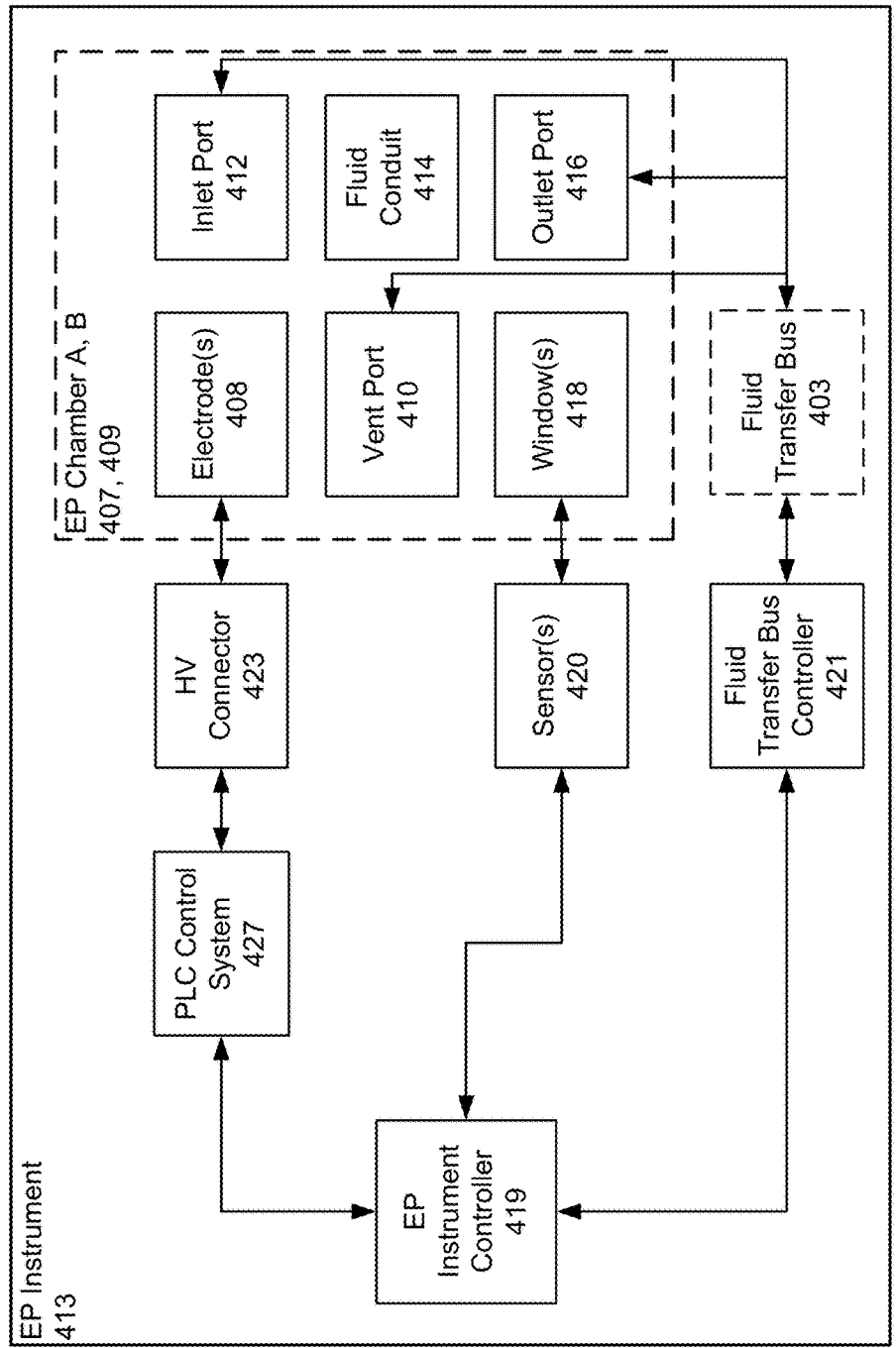
FIG. 4B is a schematic diagram of an illustrative electroporation system when the electroporation module has been coupled to the electroporation instrument.

FIG. 4B is a schematic diagram of aspects of an electroporation system, where the electroporation module of a cartridge has been coupled to the electroporation instrument 413 of a workcell. In this variation, the electroporation module comprises electroporation chambers 407, 409. The electroporation instrument 413 may comprise the electroporation instrument controller 419 that may be electrically connected to the PLC control system 427, the at least one sensor 420, and the fluid transfer bus controller 421. In embodiments, the PLC control system 427, the at least one sensor 420, and the fluid transfer bus controller 421 may be electrically connected to components contained within the electroporation chambers 407, 409. In this way, the electroporation instrument controller 419 may indirectly control at least one component within the electroporation chambers 407, 409 when the electroporation chambers 407, 409 are docked within the docking station 417 of the electroporation instrument 413. For example, the electroporation instrument controller 419 may send a signal to the fluid transfer bus controller 421 that subsequently transmits a signal to and/or controls the fluid transfer bus 403 to cause fluid flow within and between inlet port 412, vent port 410, and outlet port 416. For example, the fluid transfer bus controller 421 may send a signal to open or close each of the inlet port 412, the vent port 410, and the outlet port 416. In embodiments, the electroporation instrument controller 419 may receive a signal from one or more of the fluid transfer bus 403, the inlet port 412, the vent port 410, and the outlet port 416. For example, one or more of the inlet port 412, the vent port 410, and the outlet port 416 may send a signal indicating an open configuration, closed configuration, or partially closed configuration thereof.

In another example, the electroporation instrument controller 419 may transmit a signal to at least one sensor 420 that transmits or receives a signal via at least one window 418. For example, the at least one sensor 420 may comprise an optical sensor positioned proximal to the at least one window 418 such that the optical sensor may measure the presence or absence of fluid on the internal side of the window 418 based on reflected light.

In embodiments, the electroporation instrument controller 419 may transmit to and/or receive a signal from the PLC control system 427 that, in turn, transmits to and/or receives a signal from the high voltage connector 423. For example, the high voltage connector 423 may transmit an electrical signal to at least one electrode 408 when the cartridge, and the at least one electroporation chamber therein, is docked within the docking station. In another example, the high voltage connector 423 may receive a signal from the at least one electrode 408 of the at least one electroporation chamber 407, 409, such as a resistance value or voltage value.

The PLC control system 427 may supply a continuous or discontinuous electrical signal to the at least one electrode 408. In some embodiments, the PLC control system 427 may supply a pulsed electrical signal to the at least one electrode 408. In some embodiments, the pulsed electrical signal may have varied electrical characteristics. In some embodiments, the electrical signal may comprise between about 1 pulse and about 50 pulses, at least about 5 pulses, at least about 10 pulses, at least about 15 pulses, at least about 20 pulses, at least about 25 pulses, at least about 30 pulses, at least about 35 pulses, at least about 40 pulses, and at least about 45 pulses.

The electrical signal may comprise any suitable voltage, for example a voltage of between about 0 V and about 700 V, at least about 50 V, at least about 100 V, at least about 150 V, at least about 200 V, at least about 250 V, at least about 300 V, at least about 350 V, at least about 400 V, at least about 450 V, at least about 500 V, at least about 550 V, at least about 600 V, and at least about 650 V. It should be appreciated that the above-described range of voltages applied to the at least one electrode 408 is non-limiting and that, in many cases, the voltage applied to the at least one electrode 408 will be based on a variety of factors, including the cell solution to be electroporated (e.g., a volume of the cell solution, a type of cell within the cell solution), and the like.

In some embodiments, the electrical signal comprises a pulse width of between about 100 µs and about 1 ms, at least 100 µs, at least 200 µs, at least 300 µs, at least 400 µs, at least 500 µs, at least 600 µs, at least 700 µs, at least 800 µs, and at least 900 µs. In some embodiments, the electrical signal comprises a pulse width of between about 1 ns and about 100 µs, at least 1 ns, at least 100 ns, at least 250 ns, at least 500 ns, at least 750 ns, at least 1 µs, at least 25 µs, at least 50 µs, and at least 75 µs. The electrical signal may comprise a series of electrical pulses (constituting a pre-determined duration) with a pulse spacing between about 1 second to about 30 seconds, at least about 5 seconds, at least about 10 seconds, at least about 15 seconds, at least about 20 seconds, and at least about 25 seconds.

The electroporation system may further comprise processing circuitry, as part of (or separate from) the electroporation instrument controller 419. The processing circuitry may be configured to carry out any number of functions. For example, it may be configured to generate a first signal to flow a cell solution into the fluid conduit 414 via the inlet port 412, generate a second signal, (for example, based on data received from the at least one sensor 420), stop the flow of the cell solution into the fluid conduit 414 via the inlet port 412, generate a third signal to apply an electric field within the fluid conduit 414 for a pre-determined duration, and generate a fourth signal to flow the cell solution out of the fluid conduit 414 via the outlet port 416. In some variations, the electroporation chambers described herein comprise a vent port 410 in fluid communication with the fluid conduit 414 and arranged at the first portion of each electroporation chamber 407, 409. The electroporation chambers describe herein may further comprise a fluid pump. In some variations, the fourth signal generated by the processing circuitry may be configured to cause a fluid pump to flow the cell solution out of the fluid conduit 414 by purging the fluid conduit 414 with air via the vent port 410.

Figure 5:
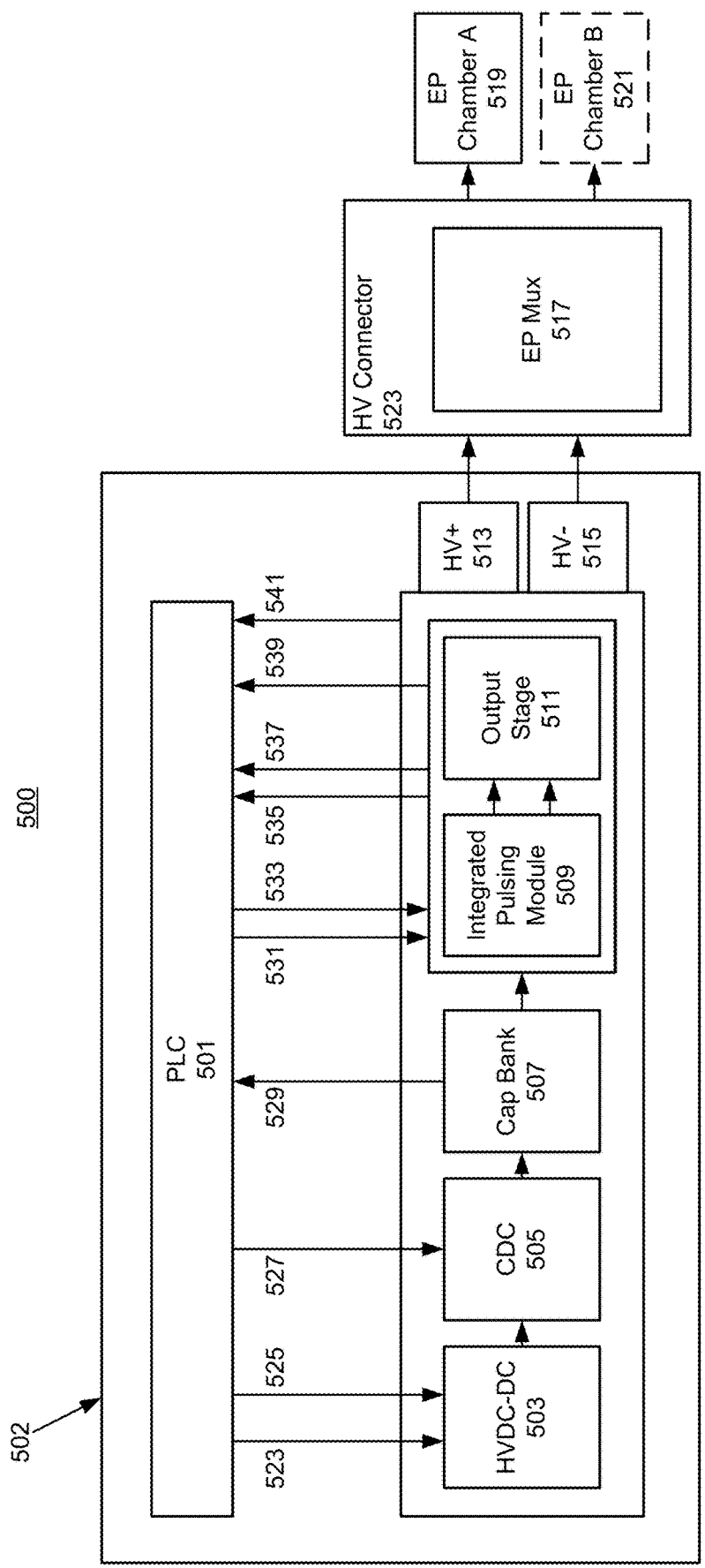
FIG. 5 is a schematic diagram of aspects of an electroporation instrument of an electroporation system.

FIG. 5 is a schematic diagram of an exemplary embodiment of an electroporation system 500. The electroporation system 500 generally provides electrical energy to at least one other component within the electroporation system. The electroporation system 500 may comprise a PLC control system 502. The PLC control system 502 may comprise a programmable logic controller ("PLC") 501. The PLC 501 may send at least one signal to at least one high-voltage DC-DC converter ("HVDC-DC") 503. For example, the PLC 501 may send a signal 523 to the HVDC-DC 503. The signal 523 may comprise an electrical signal of between 0-24 V configured to provide power to the HVDC-DC. For example, the HVDC-DC 503 may convert the 24 V input from the PLC 501 to an output of between 100-700 V. The output from the HVDC-DC 503 of between 100-700 V may charge other system components such as a capacitance bank. In an embodiment, the signal 523 may comprise an electrical signal larger than 24 V for example, at least about 25V, at least about 30 V, at least about 40 V, at least about 50 V, at least about 60 V, at least about 70 V, at least about 80 V, at least about 90 V, and at least about 100 V. The signal 423 may also comprise an amperage of 0-6.5 A. In some embodiments, the signal 523 may comprise an electrical signal larger than 6.5 A for example, at least about 7 A, at least about 8 A, at least about 9 A, and at least about 10 A. The signal 523 may be configured to turn the HVDC-DC 503 on or off. The PLC may send a separate signal 525 to the HVDC-DC 403. The signal 525 may comprise an electrical signal between 0-4.75 V. In embodiments, the signal 525 may comprise an electrical signal greater than 4.75 V such as, for example, at least about 5 V, at least about 6 V, at least about 7 V, at least about 8 V, at least about 9 V, and at least about 10 V. The signal 525 may be a variable voltage signal configured to set the voltage of the electrical signal output from the HVDC-DC 503. For instance, the signal 525 may be a particular voltage that corresponds to a particular voltage output from the HVDC-DC 503.

The electroporation system 500 may also comprise a charging/discharging circuit ("CDC") 505. The CDC 505 may comprise a switching relay. The switching relay may comprise a high watt, low resistance dumping resistor. In some embodiments, the switching relay may comprise a low watt, high resistance dumping resistor. The CDC 505 may be electrically connected to the HVDC-DC 503. The CDC 505 may be configured to receive the 100-700V output from the HVDC-DC 503. The CDC 505 may be further configured to receive a signal 527 from the PLC 501. The signal 527 may comprise an electrical signal of 0-24 V. In some embodiments, the signal 527 may enable or disable the CDC 505. The CDC 505 may be configured to output an electrical signal to at least one other component. The CDC 505 may further comprise a connection to ground.

The electroporation system 500 may also comprise a capacitance ("cap") bank 507. The cap bank 507 may be electrically connected to the CDC 505. The cap bank 507 may be configured to receive at least one electrical signal from the CDC 505. The cap bank may comprise at least one capacitor configured to be charged by the electrical signal provided by the CDC 505. The at least one capacitor may have a capacitance of at least 4.5 mF. In some embodiments, the at least one capacitor may have a capacitance of at least about 0.5 mF, at least about 1 mF, at least about 1.5 mF, at least about 2 mF, at least about 2.5 mF, at least about 3 mF, at least about 3.5 mF, at least about 4 mF, at least about 5.5 mF, at least about 6 mF, at least about 6.5 mF, at least about 7 mF, at least about 7.5 mF, at least about 8 mF, at least about 8.5 mF, at least about 9 mF, at least about 9.5 mF, and at least about 10 mF. In some embodiments, the cap bank 407 may comprise multiple capacitors that each have a capacitance of at least 4.5 mF. Once the cap bank 507 reaches it maximum capacitance level, the CDC 505 may be configured to discharge or shunt the energy stored in the cap bank 507 to ground.

The cap bank 507 may also be electrically connected to the PLC 501. The cap bank 507 may be configured to send a signal 529 to the PLC 401. The signal 529 may comprise an electrical signal between about 1 V and 100 V. In some embodiments, the signal 529 may be used to read the voltage of the cap bank 507. The cap bank 507 may further comprise a connection to ground.

The electroporation system 500 allows for switching polarities of an electric load applied to the electroporation chamber to improve efficiency of the electroporation process. To this end, the electroporation system 500 comprises an integrated pulsing module 509, which opens and closes the load path, and an output stage 511, which is an electric circuit that switches the polarity of the voltage output from the integrated pulsing module 509. In some embodiments, the output stage 511 sends the output voltage to a positive high voltage lead 513 and a negative high voltage lead 515. The cap bank 507 may be electrically connected to the integrated pulsing module 509. The integrated pulsing module 509 may comprise a switch array. The switch array may be configured to turn on the release path to the output stage 511. For example, the switch array may have an initial configuration that prevents any charge output by the integrated pulsing module from reaching the output stage 511. The switch array may have an additional configuration that allows a charge output by the integrated pulsing module to reach the output stage 511. The output stage 511 may comprise an H-bridge configured to allow switching of the output polarity. For example, the polarity of the output signal transmitted to one of the electrodes (e.g., first electrode 308A and second electrode 308B of FIG. 3A) may be switched from positive to negative, or negative to positive. In other words, in some variations, the first electrode 308A may be an anode and the second electrode 308B may be a cathode. In a first instance, a positive electrical signal may be transmitted from the output stage 511 to the cathode 308B and a negative electrical signal may be transmitted to the anode 308A. Switching the polarities of the electrical signals transmitted by the output stage 511 may result in, in a second instance, the anode 308A receiving a positive electrical signal and the cathode 308B receiving a negative electrical signal.

The output polarity may be switched during an application of electrical energy to a cell solution. For example, the cell solution may be initially treated by electrical energy to electroporate the cells from a first direction. The polarity of the electrical energy may then be switched to electroporate the cells from a second direction. The polarity of the electrical energy may be switched to improve the efficiency of the electroporation treatment.

The output stage 511 may be configured to support an output signal up to 880 A. In embodiments, the output stage 511 may output a signal of at least about 100 A, at least about 200 A, at least about 300 A, at least about 400 A, at least about 500 A, at least about 600 A, at least about 700 A, at least about 800 A, at least about 900 A, and at least about 1000 A. The output signal from the output stage 511 may also comprise at least one pulse. The at least one pulse may comprise a pulse width up to and including 1 ms. In embodiments, the pulse width of the output signal from the output stage 511 may be at least 100 µs, at least 200 µs, at least 300 µs, at least 400 µs, at least 500 µs, at least 600 µs, at least 700 µs, at least 800 µs, and at least 900 µs. In some embodiments, the at least one pulse width may be between 100 µs and 5 ms.

At least one of the integrated pulsing module 509 and output stage 511 may be configured to receive at least one input signal from the PLC 501. For example, one of the integrated pulsing module 509 and output stage 511 may receive at least one of signals 531 and 533. In some embodiments, the signal 531 may be a negative power signal. In some embodiments, the signal 533 may be a positive power signal. One of the integrated pulsing module 509 and output stage 511 may also be configured to send at least one signal to the PLC 501. For example, the integrated pulsing module 509 may send at least one of signals 535, 537, and 539 to the PLC 501. In some embodiments, the signal 535 may be a positive high voltage read signal. In some embodiments, the signal 537 may be a negative high voltage read signal. In some embodiments, the signal 539 may comprise a shunt voltage signal.

The electroporation system 500 may also comprise at least electrical output lead. The at least one electrical output lead may comprise a positive high voltage lead 513 and a negative high voltage lead 515. Of course, the nomenclature used for the high voltage leads 513, 515 is representative, as the polarity of the leads may be switched such that high voltage lead 513 is a negative lead and high voltage lead 515 is a positive lead. The leads 513 and 515 may be electrically connected to the output stage 511. The leads 513 and 515 may be further electrically connected to a high voltage connector 523. The high voltage connector 523 may comprise a multiplexer 517. The multiplexer 517 may be electrically connected to at least one electroporation flow chamber. For example, the multiplexer 517 may be electrically connected to an electroporation chamber A 519 and electroporation chamber B 521.

H. Methods of Electroporating Cells

Figure 6:
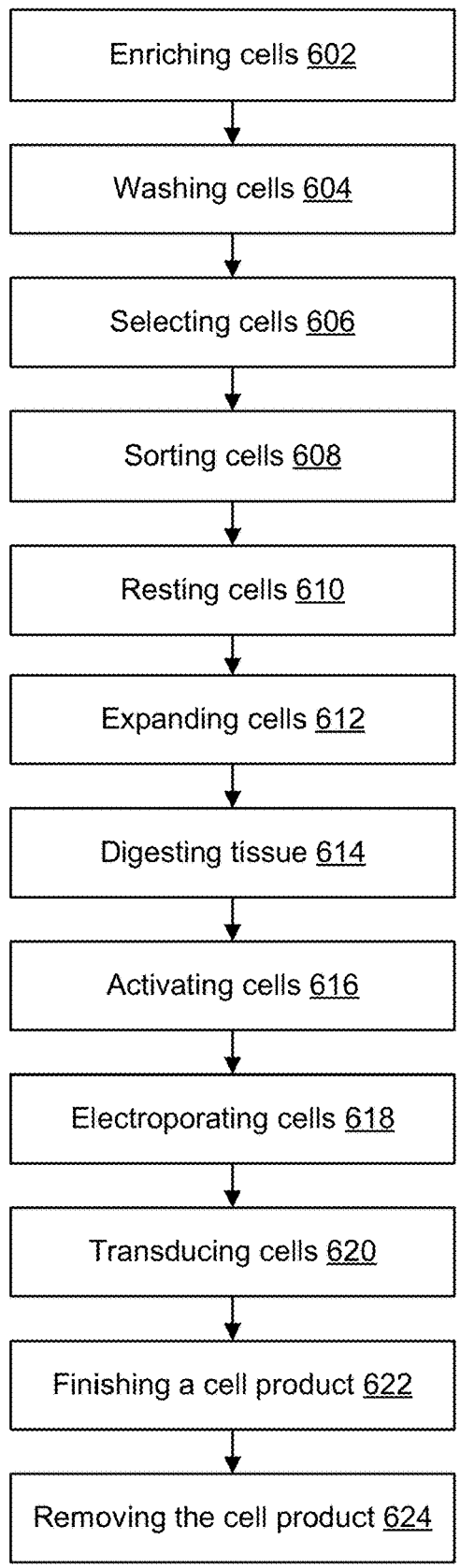
FIG. 6 is a flowchart of an illustrative variation of a method of cell processing.

Generally, the systems and devices described herein may perform one or more cell processing steps to manufacture a cell product. FIG. 6 is a flowchart of an illustrative method of cell processing 600 that can be performed via the systems and devices described above. The method 600 may include enriching a selected population of cells in a solution (e.g., fluid) in a step 602. For example, the solution may be conveyed to a CCE module of a cartridge via a fluid transfer bus. A robot may be operated to move the cartridge to a CCE instrument so that the CCE module interfaces with the CCE instrument. The CCE instrument may be operated to cause the CCE module to enrich the selected population of cells. Additionally, or alternatively, the cell product may be introduced into and out of the cartridge via a sterile liquid transfer port (either manually or automatically) for any of the steps described herein. In some embodiments, the cartridge may be sterilized in a feedthrough port (either manually or automatically).

In some embodiments, a selected population of cells in the solution may be washed 604. For example, the solution may be conveyed to the CCE module of the cartridge via the fluid transfer bus. A robot may be operated to move the cartridge to the CCE instrument so that the CCE module interfaces with the CCE instrument. The CCE instrument may be operated to cause the CCE module to remove media from the solution, introduce media into the solution, and/or replace media in the solution.

In some embodiments, a population of cells in the solution may be selected in a step 606. For example, the solution may be conveyed to a selection module of the cartridge via the fluid transfer bus. The robot may be operated to move the cartridge to a selection instrument so that the selection module interfaces with the selection instrument. The selection instrument may be operated to cause the selection module to select the selected population of cells.

In some embodiments, a population of cells in the solution may be sorted in a step 608. For example, the solution may be conveyed to a sorting module of the cartridge via the fluid transfer bus. The robot may be operated to move the cartridge to a sorting instrument so that the sorting module interfaces with the sorting instrument. The sorting instrument may be operated to cause the sorting module to sort the population of cells.

In some embodiments, the solution may be conveyed to a bioreactor module of the cartridge via the fluid transfer bus to rest in a step 610. For example, the robot may be operated to move the cartridge to a bioreactor instrument so that a bioreactor module interfaces with the bioreactor instrument. The bioreactor instrument may be operated to cause the bioreactor module to maintain the cells at a set of predetermined conditions.

In some embodiments, the cells may be expanded in the solution in a step 612. For example, the solution may be conveyed to the bioreactor module of the cartridge via the fluid transfer bus. The robot may be operated to move the cartridge to the bioreactor instrument so that the bioreactor module interfaces with the bioreactor instrument. The bioreactor instrument may be operated to cause the bioreactor module to expand the cells by cellular replication.

In some embodiments, tissue may be digested by conveying an enzyme reagent via the fluid transfer bus to a module containing a solution containing a tissue such that the tissue releases a select cell population into the solution in a step 614.

In some embodiments, a selected population of cells in the solution may be activated by conveying an activating reagent via the fluid transfer bus to a module containing the solution containing the cell product in a step 616.

In some embodiments, the solution may be conveyed to an electroporation module of the cartridge via the fluid transfer bus and receive an electroporation signal to electroporate the cells in the solution in a step 618. For example, the robot may be operated to move the cartridge to an electroporation instrument so that the electroporation module interfaces with the electroporation instrument. The electroporation instrument may be operated to cause the electroporation module to electroporate the selected population of cells in the presence of genetic material.

In some embodiments, an effective amount of a vector may be conveyed via the fluid transfer bus to a module containing the solution containing the cell product, thereby transducing a selected population of cells in the solution in a step 620.

In some embodiments, a formulation solution may be conveyed via the fluid transfer bus to a module containing the cell product to generate a finished cell product in a step 622. For example, the finished cell product may be conveyed to one or more product collection bags. In some embodiments, finishing a cell product may comprise one or more steps of washing cells, concentrating cells, exchanging a buffer of the cells with a formulation buffer, and dosing cells in the formulation buffer in predetermined quantities into one or more product collection bags and/or vessels.

In some embodiments, the cell product may be removed, either manually or automatically, from the cartridge to harvest the cells in a step 624.

In some embodiments, the cell product may comprise one or more of an immune cell genetically engineered chimeric antigen receptor T cell, a genetically engineered T cell receptor (TCR) cell, a hematopoietic stem cell (HSC), and a tumor infiltrating lymphocyte (TIL). In some embodiments, the immune cell may comprise a natural-killer (NK) cell.

Any of the electroporation systems and devices described above may be used in carrying out the electroporation methods. For example, with reference to the electroporation of a cell solution described in step 618 above, the method of electroporating cells may comprise flowing a cell solution into a fluid conduit of an electroporation chamber via an inlet port, detecting, via at least one window, a presence of the cell solution at a first portion of the electroporation chamber, ceasing flow of the cell solution into the fluid conduit, applying an electric field to the cell solution within the fluid conduit for a pre-determined duration via a first electrode and a second electrode, and flowing the cell solution out of the fluid conduit via an outlet port. In some embodiments, the at least one window may be a first window arranged proximate the outlet port.

The method may further comprise detecting, via a second window and after detecting the presence of the cell solution at the first portion of the electroporation chamber via the first window, a presence of the cell solution at the second portion of the electroporation chamber, wherein the electric field is applied after detecting the presence of the cell solution at the second portion of the electroporation chamber. In some embodiments, detecting the presence of the cell solution at the second portion of the electroporation chamber comprises detecting a presence of the cell solution proximate a vent port in fluid communication with the fluid conduit and arranged at the second portion of the electroporation chamber. In some embodiments, detecting the presence of the cell solution at the first end of the electroporation chamber comprises detecting a presence of the cell solution proximate an auxiliary channel extending from the fluid conduit, the auxiliary channel being in fluid communication with the fluid conduit and the outlet port. In some embodiments, flowing the cell solution out of the fluid conduit via the outlet port comprises purging the fluid conduit with air via a vent port in fluid communication with the fluid conduit and arranged at the second portion of the electroporation chamber.

FIG. 7A provides a flow diagram describing an illustrative method 701 of cell electroporation. Method 701 can be controlled by an electroporation instrument controller (see 419 of FIG. 4A). In a step 705 of method 701, a signal may be generated to flow fluid (e.g., cell solution) into a fluid conduit of an electroporation chamber via an inlet port at a second portion of the electroporation chamber. For example, fluid may flow through the inlet port, through an auxiliary channel, and into the fluid conduit. The quantity of fluid in the fluid conduit may be determined in a step 710. For example, a sensor proximate to a window may determine the presence or absence of fluid within the fluid conduit and/or auxiliary channel. If the sensor proximate to the window detects the presence of fluid, the volume of fluid contained with the fluid conduit of the electroporation chamber may be estimated based on the known dimensions of the fluid conduit, auxiliary channels, and plurality of ports, and the location of the sensor relative to those dimensions. The volume of fluid within the fluid conduit may then help inform how much voltage and/or current to apply to the cell solution to accomplish the electroporation.

At step 715, a signal may be generated to stop the flow of fluid into the fluid conduit. For example, fluid may be stopped by stopping a fluid pump used to pump fluid into the inlet port. In some embodiments, fluid flow may be stopped by closing the inlet port in response to a signal. The outlet port may also be closed. The vent port may be open, closed, or partially open or closed. Then, a signal may be generated to apply electrical energy to the fluid contained within the fluid conduit to electroporate the cells in a step 720. In some embodiments, the electrical energy may also electroporate the cells contained within at least one auxiliary channel. In a step 725, a signal may be generated to flow fluid within the fluid conduit out of the fluid conduit via the outlet port. The fluid may begin flowing out of the fluid conduit by opening the outlet port. The fluid may flow out of the fluid conduit to the outlet port via an auxiliary channel fluidically connected to the fluid outlet.

FIG. 7B provides a flow diagram describing another suitable method 702 of cell electroporation, where the quantity of fluid in the fluid conduit is determined using multiple sensors. Method 702 can be controlled by an electroporation instrument controller (see 419 of FIG. 4A). In a step 705, a signal may be generated to flow fluid into a fluid conduit of an electroporation chamber via an inlet port at a second portion of the electroporation chamber. For example, fluid may flow through the inlet port, through an auxiliary channel, and into the fluid conduit. In a step 706, the presence or absence of fluid may be detected by at least one sensor proximate to a second portion of the electroporation chamber. For example, at least one sensor proximate to the second portion may determine the presence or absence of fluid within the fluid conduit and/or auxiliary channel. In a step 707, the presence or absence of fluid may be detected by another sensor proximate to the first portion of the electroporation chamber. In this way, when measurements from both sensors indicate the presence of fluid in both of the first portion and the second portion of the fluid conduit, the volume of fluid within the fluid conduit may be estimated based on the known dimensions of the fluid conduit, auxiliary channels, and plurality of ports, and the relative location of each of the at least two sensors to those dimensions.

The estimated volume of fluid within the fluid conduit may then determine the electrical characteristics of the electrical energy, such as voltage and current, used to electroporate the cell solution contained therein. Then, a signal may be generated at step 715 to stop the flow of fluid into the fluid conduit. For example, fluid may be stopped by stopping a fluid pump used to pump fluid into the inlet port. In embodiments, fluid flow may be stopped by closing the inlet port in response to a signal. The outlet port may also be closed. The vent port may be open or closed. Then, a signal may be generated to apply electrical energy to the fluid contained within the fluid conduit to electroporate the cells in a step 720. In some embodiments, the electrical energy may also electroporate the fluid contained within at least one auxiliary channel. A signal may be generated at step 725 to flow the fluid in the fluid conduit out of the fluid conduit. The fluid may begin flowing out of the fluid conduit by opening the outlet port. The fluid may flow out of the fluid conduit to the outlet port via an auxiliary channel fluidically connected to the outlet port.

Figure 7C:
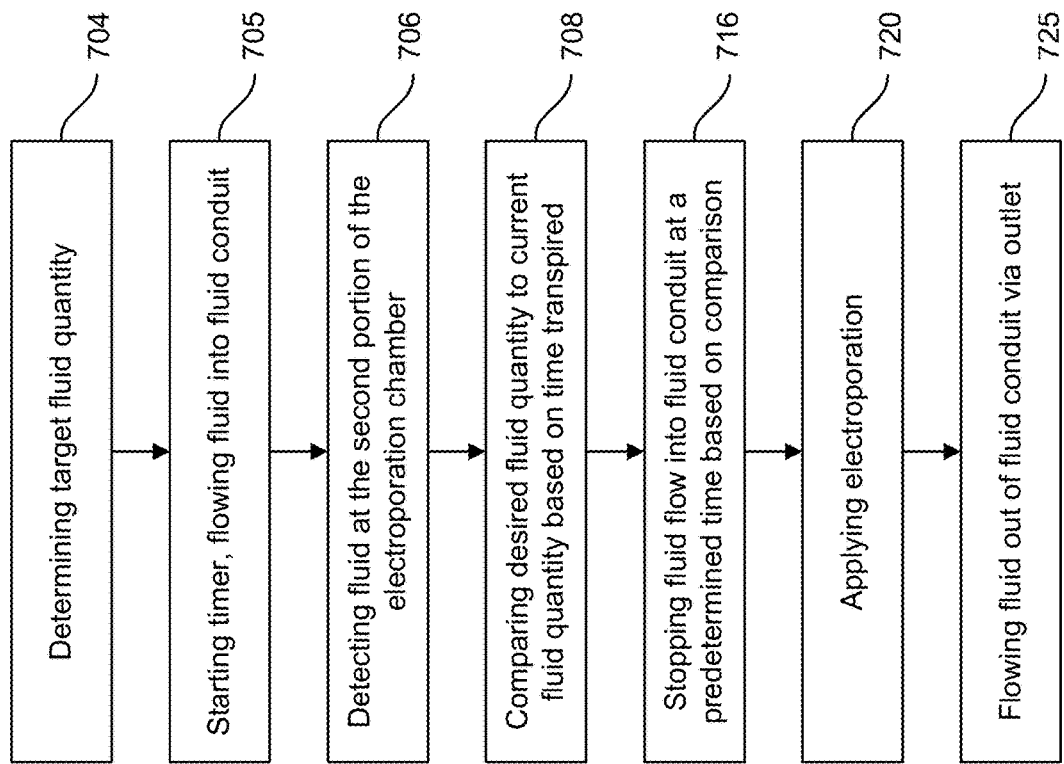

FIG. 7C provides a flow diagram describing another suitable method 703 of cell electroporation. Like above, method 703 can be controlled by an electroporation instrument controller (see 419 of FIG. 4A). However, unlike previous methods, method 703 integrates the use of a timer. In an initial configuration, the inlet port of the electroporation chamber is closed, and the outlet port and vent port of the electroporation chamber are open. In a step 704, a target volume of fluid to be electroporated within the fluid conduit may be obtained or determined. Based on the target volume, the time of fluid flow required to fill the fluid conduit to the target volume can be estimated. For example, the estimated fill time may be based on parameters such as (1) a size (e.g., diameter) of the fluid tubing coupling the fluid transfer bus to the inlet port, (2) properties of the fluid such as density, temperature, pressure, and (3) the velocity of the fluid within the fluid tubing coupling the fluid transfer bus to the inlet port. Knowing these parameters, an estimated flow rate (e.g., μl/s) of fluid flow through the inlet port, through the auxiliary channel, and into the fluid conduit of the electroporation chamber can be estimated, and a comparison of this flow rate with the target volume results in the estimated fill time.

In some variations, the initial volume contained within the electroporation chamber may also be determined. For example, at least one sensor may determine the presence or absence of fluid in any portion of the fluid conduit, auxiliary channels, and plurality of ports. If a first sensor detects the presence of fluid, the known dimensions of the fluid conduit, auxiliary channels, and plurality of ports may be used to estimate the volume of fluid contained therein based on the relative location of the sensor to those dimensions. Based on that initial determination, the target volume may represent a delta between the initial volume and target volume.

Subsequently, at step 705, a signal may be generated to open the inlet port, thereby allowing fluid flow through the inlet port, through an auxiliary channel fluidly connected to the inlet port, and into the fluid conduit, and a timer is started. The timer is started concurrently with the opening of the inlet port. As the fluid flows into the fluid conduit, a sensor proximal to the second portion (e.g., an optical sensor proximal to the first window) of the electroporation chamber may detect the presence of fluid therein in a step 706. Concurrently with the detection of the presence of fluid by the sensor proximal to the second portion, an electrical signal is sent to the outlet port to close the outlet port. At step 708, an elapsed time is compared to the estimated fill time. When the elapsed time equals the estimated fill time, the flow of fluid through the inlet port may be stopped at step 716 and in response to a generated signal. For example, fluid may be stopped by stopping a fluid pump used to pump fluid into the inlet port and/or by closing the inlet port in response to a signal transmitted thereto. The outlet port may also be closed. The vent port may be open, closed, or partially open. A signal may be generated to apply an electric field via the electrodes to the fluid contained within the fluid conduit to electroporate the cells in a step 720. In embodiments, the electric field may also electroporate the cells contained within at least one auxiliary channel. After electroporation, a signal may be generated to flow the fluid in the fluid conduit out of the fluid conduit in a step 725. The fluid may begin flowing out of the fluid conduit by opening the outlet port. The fluid may flow out of the fluid conduit to the outlet port via an auxiliary channel fluidically connected to the fluid outlet.

FIG. 8A provides a flow diagram of yet another suitable method 801 of cell electroporation, wherein the presence of fluid is determined by sensors proximal to the inlet port and vent port, and wherein excess fluid may be expelled prior to the application of electroporation energy to a cell solution. As above, method 801 can be controlled by an electroporation instrument controller (see 419 of FIG. 4A). In an initial configuration, the inlet port and outlet port of the electroporation chamber is closed, and the vent port of the electroporation chamber is open. Then, at step 805, the presence or absence of fluid may be detected by a first sensor proximal to the inlet port. Then, at step 810, the inlet port may be opened to begin flowing fluid through the inlet port, through an auxiliary channel fluidly connected thereto, and into the fluid conduit. While the fluid is flowing into the fluid conduit, the presence of fluid may or may not be detected at a second sensor in a step 815. The second sensor may be proximal to the vent port. In particular, detecting fluid at the second sensor at step 815 indicates a volume of fluid contained within the electroporation chamber that exceeds a maximum volume of the fluid conduit. The excess fluid may flow out of the fluid conduit in a step 820. For example, the excess fluid may flow through an auxiliary channel and through the inlet port. In some embodiments, the excess fluid may flow through the inlet port by a negative pressure applied to the fluid conduit and/or by an air purge applied to the fluid conduit via the vent port. Subsequently, the second sensor may detect the absence of fluid in a step 825. As long as the second sensor detects the presence of fluid, excess fluid may continue to flow through the inlet port. When fluid is no longer detected at the second sensor, the flow of fluid out of the fluid conduit via the inlet port may be stopped in a step 830.

If fluid is not detected at the second sensor in a step 815, the flow of fluid into the fluid conduit may be stopped in a step 830. For example, a fluid pump within the fluid transfer bus that is configured to pump fluid into the inlet port may be turned off. In another example, the inlet port may be closed to prevent fluid flow therethrough.

The presence or absence of fluid detected by at least one sensor may determine the volume of fluid within the fluid conduit. For example, if fluid flow into the fluid conduit is stopped prior to the sensor proximal to the vent port detecting the presence of fluid, the known volume of the fluid conduit, auxiliary channels, and plurality of ports may be used to estimate the volume of fluid contained therein, similarly to aspects of the methods of FIG. 7A and FIG. 7C. In another example, where fluid is detected by the sensor proximate to the vent port at step 815 and excess fluid must be removed at step 820, the change in sensor output from detecting the presence of fluid to detecting the absence of fluid at step 825 may help to define a volume of fluid contained within the fluid conduit.

The volume of fluid within the fluid conduit may then determine the electrical characteristics of the electrical energy, such as voltage and current, used to electroporate the cell solution contained therein. In a step 835, electrical energy may be applied to the fluid contained within the fluid conduit to electroporate the cells therein. The electrical energy may also electroporate the cells contained within at least one auxiliary channel. Then, the fluid in the fluid conduit may flow out of the fluid conduit via an outlet port in a step 840. The fluid may begin flowing out of the fluid conduit by opening the outlet port. The fluid may flow out of the fluid conduit to the outlet port via an auxiliary channel fluidically connected to the fluid outlet and fluid conduit.

Figure 8B:
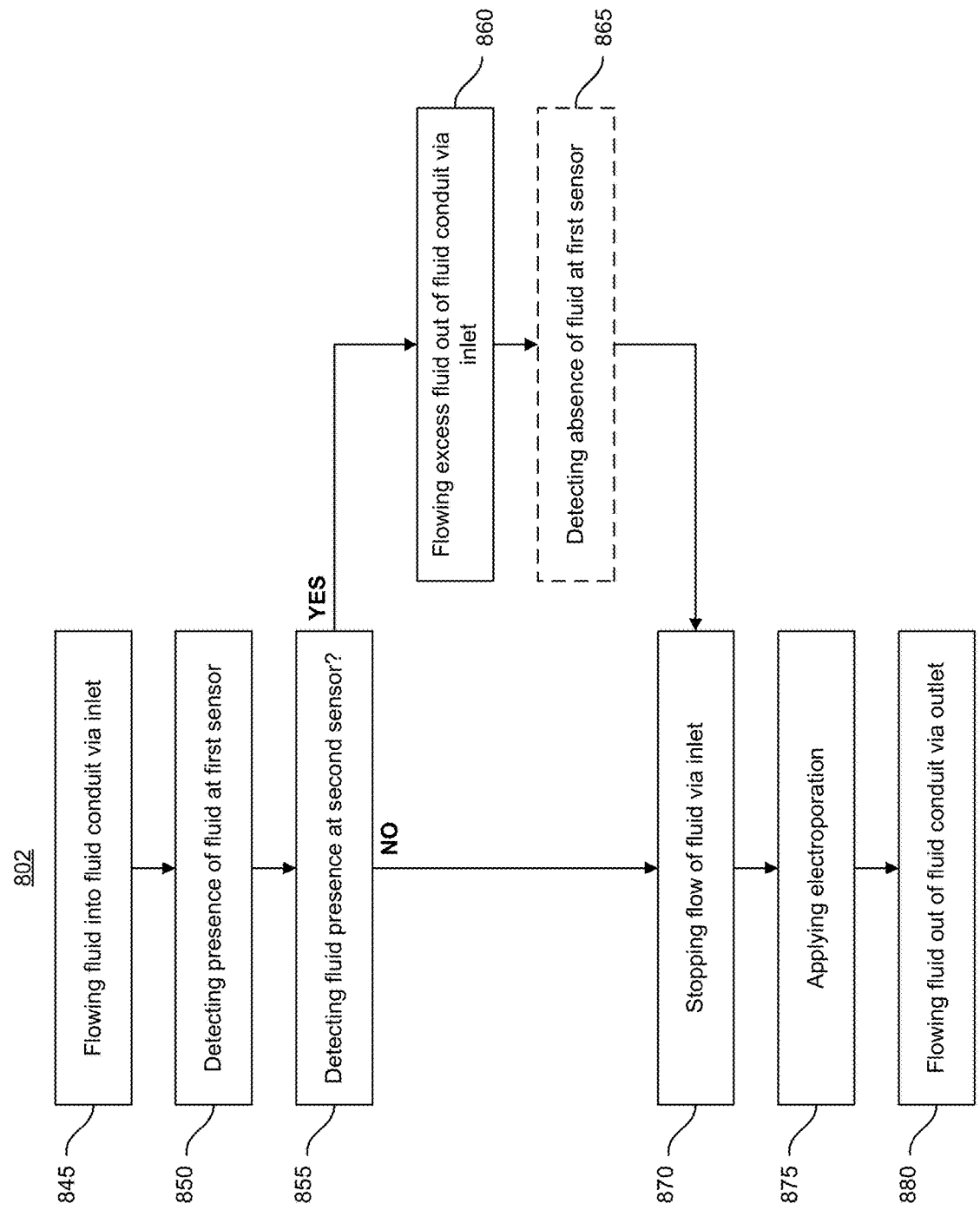

FIG. 8B provides a flow diagram describing another suitable method 802 of cell electroporation as described herein, wherein the presence of fluid is determined by sensors within a first window and a second window of the electroporation chamber, and wherein excess fluid may be expelled prior to the application of electroporation energy to a cell solution. As above, method 802 can be controlled by an electroporation instrument controller (see 419 of FIG. 4A). In an initial configuration, the inlet port and outlet port of the electroporation chamber are closed, and the vent port of the electroporation chamber is open. Then, fluid may begin flowing through an inlet port of the electroporation chamber, through an auxiliary channel fluidly coupled to the inlet port, and into the fluid conduit of the electroporation chamber in a step 845.

Then, in a step 850, the presence or absence of fluid may be detected by a first sensor in a first portion. For example, a first sensor proximate to the first window in the first portion of the electroporation chamber may determine the presence of fluid within the fluid conduit and/or auxiliary channel. In a step 855, the presence of fluid may or may not be detected at a second sensor in a step 855. The second sensor may be proximate to the second window in a second portion of the electroporation chamber. If fluid is detected at the second sensor the step 855, a volume of fluid contained within the electroporation chamber exceeds a maximum volume of the fluid conduit. Accordingly, the excess fluid may flow out of the fluid conduit in a step 860. For example, excess fluid may be flowed out of the fluid conduit via the inlet port. Subsequently, the second sensor may detect an absence of fluid in a step 865. If the second sensor continues to detect the presence of fluid, excess fluid may continue to flow from the fluid conduit and out the inlet port. Once the second sensor detects the absence of fluid, the flow of excess fluid out of the fluid may be stopped.

If fluid is not detected by the second sensor in a step 855, the flow of fluid into the fluid conduit may be stopped in a step 870. The flow of fluid may be stopped by closing the inlet port. In an embodiment, the flow of fluid may be stopped by turning off a fluid pump within the fluid transfer bus that is configured to pump fluid into the inlet port. The presence or absence of fluid detected by at least one sensor may help to determine the volume of fluid within the fluid conduit. For example, if fluid flow into the fluid conduit is stopped prior to the second sensor proximal to the second window detecting the presence of fluid, the known volume of the fluid conduit, auxiliary channels, and plurality of ports may be used to estimate the volume of fluid contained therein, similarly to aspects of the methods of FIG. 7A and FIG. 7C. In another example, where fluid is detected by the second sensor proximate to the second window at step 855 and excess fluid must be removed at step 860, the change in sensor output from detecting the presence of fluid to detecting the absence of fluid at step 855 may help to define a volume of fluid contained within the fluid conduit.

The volume of fluid within the fluid conduit, auxiliary channels, and plurality of ports may then determine the electrical characteristics of the electrical energy, such as voltage and current, used to electroporate the cell solution contained therein. In a step 875, electrical energy may be applied to the fluid contained within the fluid conduit to electroporate the cells therein. The electrical energy may also electroporate the cells contained within at least one auxiliary channel. Then, the fluid in the fluid conduit may flow out of the fluid conduit via an outlet port in a step 880. The fluid may flow out of the fluid conduit through an auxiliary channel fluidically connected to the fluid outlet and fluid conduit.

While described above as containing certain steps, it should be understood that the methods of cell processing may include any subset of cell processing steps in any suitable order.

All references cited are herein incorporated by reference in their entirety.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electroporation chamber, comprising:
a first electrode and a second electrode;
a plurality of ports comprising
an inlet port at a first portion of the electroporation chamber, and
an outlet port at a second portion of the electroporation chamber;
a fluid conduit arranged between the first electrode and the second electrode, the fluid conduit being in fluid communication with the inlet port, the outlet port, and each of a plurality of ports via auxiliary channels extending therefrom; and
at least one window disposed on a wall of the electroporation chamber and providing a view to a segment of the fluid conduit,
wherein the at least one window comprises a first window and a second window, the first window having a view to a first segment of the fluid conduit and the second window having a view to a second segment of the fluid conduit, and wherein the second window is proximate a first auxiliary channel of the plurality of auxiliary channels that is in fluid communication with the outlet port.

2. The electroporation chamber of claim 1, wherein the plurality of ports further comprises
a vent port in fluid communication with the fluid conduit and arranged at the first portion of the electroporation chamber.

3. The electroporation chamber of claim 1, wherein the fluid conduit has a volume defined by a distance between the first electrode and the second electrode.

4. The electroporation chamber of claim 3, wherein the volume of the fluid conduit is between about 0.5 µL to about 2.5 mL.

5. The electroporation chamber of claim 1, wherein a distance between the first electrode and the second electrode is between about 0.5 mm and about 5 mm.

6. The electroporation chamber of claim 1, further comprising a first housing and a second housing, wherein the first electrode, the fluid conduit, and the second electrode are positioned between the first housing and the second housing.

7. The electroporation chamber of claim 1, wherein the segment of the fluid conduit is proximate the first portion of the electroporation chamber.

8. The electroporation chamber of claim 1, wherein the segment of the fluid conduit is proximate the second portion of the electroporation chamber.

9. The electroporation chamber of claim 1, wherein the at least one window comprises a first window and a second window, the first window having a view to a first segment of the fluid conduit and the second window having a view to a second segment of the fluid conduit.

10. The electroporation chamber of claim 2, wherein the fluid conduit is in fluid communication with each of the plurality of ports via auxiliary channels extending therefrom.

11. The electroporation chamber of claim 10, wherein each of the auxiliary channels is fluidically coupled the fluid conduit and a respective one of the plurality of ports.

12. The electroporation chamber of claim 11, wherein an auxiliary channel of the auxiliary channels fluidically coupling the fluid conduit to the outlet port is curvilinear.

13. The electroporation chamber of claim 11, wherein an auxiliary channel in fluid communication with the outlet port is curvilinear, and wherein the second window is proximate the curvilinear auxiliary channel.

14. The electroporation chamber of claim 13, wherein the second window is proximate a base of the curvilinear auxiliary channel.

15. The electroporation chamber of claim 11, wherein the first window is proximate the auxiliary channel in fluid communication with the vent port.

16. The electroporation chamber of claim 15, wherein the first window is proximate a base of the auxiliary channel in fluid communication with the vent port.

17. The electroporation chamber of claim 2, wherein the inlet port arranged at the first portion of the electroporation chamber is further arranged toward a first side wall of the electroporation chamber, and wherein the vent port arranged at the first portion of the electroporation chamber is further arranged toward a second side wall of the electroporation chamber.

18. The electroporation chamber of claim 4, wherein, along an axis defined from the first portion of the electroporation chamber to the second portion of the electroporation chamber, the fluid conduit has a triangular cross-section.

19. The electroporation chamber of claim 1, wherein each of the plurality of ports extends through the first electrode and/or the second electrode.

20. An electroporation chamber, comprising:
a first electrode and a second electrode;
a plurality of ports comprising
an inlet port at a first portion of the electroporation chamber and arranged toward
a first side wall of the electroporation chamber,
an outlet port at a second portion of the electroporation chamber; and
a vent port at the first portion of the electroporation chamber and arranged toward
a second side wall of the electroporation chamber;
a fluid conduit arranged between the first electrode and the second electrode, the fluid conduit being in fluid communication with the inlet port, the outlet port, and the vent port; and
at least one window disposed on a wall of the electroporation chamber and providing a view to a segment of the fluid conduit.

21. The electroporation chamber of claim 20, wherein the fluid conduit has a volume defined by a distance between the first electrode and the second electrode.

22. The electroporation chamber of claim 21, wherein the volume of the fluid conduit is between about 0.5 µL to about 2.5 mL.

23. The electroporation chamber of claim 20, wherein a distance between the first electrode and the second electrode is between about 0.5 mm and about 5 mm.

24. The electroporation chamber of claim 20, further comprising a first housing and a second housing, wherein the first electrode, the fluid conduit, and the second electrode are positioned between the first housing and the second housing.

25. The electroporation chamber of claim 20, wherein the segment of the fluid conduit is proximate the first portion of the electroporation chamber.

26. The electroporation chamber of claim 20, wherein the segment of the fluid conduit is proximate the second portion of the electroporation chamber.

27. The electroporation chamber of claim 20, wherein the at least one window comprises a first window and a second window, the first window having a view to a first segment of the fluid conduit and the second window having a view to a second segment of the fluid conduit.

\* \* \* \* \*